US009758779B2

(12) United States Patent
Jostock et al.

(10) Patent No.: US 9,758,779 B2
(45) Date of Patent: Sep. 12, 2017

(54) CELL SURFACE DISPLAY OF POLYPEPTIDE ISOFORMS BY STOP CODON READTHROUGH

(75) Inventors: Thomas Jostock, Neuenburg am Rhein (DE); Hans-Peter Knopf, Schallstadt (DE); Burkhard Wilms, Weil am Rhein (DE); Audrey Nommay, Blotzheim (FR)

(73) Assignee: Novartis AG, Basel (CH)

( * ) Notice: Subject to any disclaimer, the term of this patent is extended or adjusted under 35 U.S.C. 154(b) by 1046 days.

(21) Appl. No.: 13/060,974

(22) PCT Filed: Aug. 28, 2009

(86) PCT No.: PCT/EP2009/006246
§ 371 (c)(1),
(2), (4) Date: May 13, 2011

(87) PCT Pub. No.: WO2010/022961
PCT Pub. Date: Mar. 4, 2010

(65) Prior Publication Data
US 2011/0281751 A1    Nov. 17, 2011

(30) Foreign Application Priority Data
Aug. 28, 2008 (EP) .................................. 08163161

(51) Int. Cl.
*C12P 21/06* (2006.01)
*C12P 21/04* (2006.01)
*C12N 15/10* (2006.01)

(52) U.S. Cl.
CPC .... *C12N 15/1037* (2013.01); *C07K 2319/035* (2013.01)

(58) Field of Classification Search
CPC ...................... C12N 15/1037; C07K 2319/035
See application file for complete search history.

(56) References Cited

U.S. PATENT DOCUMENTS

| 2003/0033616 | A1   | 2/2003  | Star-Lack |
|--------------|------|---------|-----------|
| 2003/0118592 | A1   | 6/2003  | Ledbetter |
| 2005/0059082 | A1   | 3/2005  | Breitling |
| 2005/0136049 | A1   | 6/2005  | Ledbetter |
| 2007/0224635 | A1 * | 9/2007  | Bouquin ........................ 435/7.1 |
| 2013/0338038 | A1 * | 12/2013 | DuBridge et al. ............. 506/10 |

FOREIGN PATENT DOCUMENTS

| EP | 1605058 A1 | 12/2005 | |
| WO | 9104055 | 4/1991 | |
| WO | 94/10317 A2 | 5/1994 | |
| WO | 03/014361 | 2/2003 | |
| WO | 2005/073375 | 8/2005 | |
| WO | WO 2005/073375 | * 8/2005 | ............. C12N 15/10 |
| WO | WO2007131774 | * 11/2007 | ............. C12N 15/28 |

OTHER PUBLICATIONS

Anderson Stacie M. et al: "Intercellular transfer of a glycosylphosphatidylinositol (GPI)-linked protein: release and uptake of CD4-GPI from recombinant adeno-associated virus-transduced HeLa cells", Proc. Natl. Acad. Sci. USA, 93:5894-5898, Jun. 1996.
Chatterjee S. et al: "The GPI-anchor and protein sorting", CMLS Cellular and Molecular Life Sciences, 58:1969-1987, 2001.
Mendelson Karen et al: "Stimulation of platelet-derived growth factor receptor beta (PDGFR beta) activates ADAM17 and promotes metalloproteinase-dependent cross-talk between the PDGFR beta and epidermal growth factor receptor (EGFR) signaling pathways", The Journal of Biological Chemistry, 285(32): 25024-25032, Aug. 6, 2010.
Paulick Margot G. et al: "The glycosylphosphatidylinositol anchor: a complex membrane-anchoring structure for proteins", Biochemistry 2008, 47, 6991-700.
Taylor David R. et al: "GPI-anchored proteins in health and disease", Protein Reviews, 13:39-55, 2011.
Williams I et al: "Genome-wide prediction of stop codon readthrough during translation in the yeast *Saccharomyces cerevisiae*", Nucleic Acids Research, vol. 32, No. 22, 2004, pp. 6605-6616.
Namy Olivier et al: "Identification of stop codon readthrough genes in *Saccharomyces cerevisiae*", Nucleic Acids Research, vol. 31, No. 9 May 1, 2003 (May 1, 2003), pp. 2289-2296.
Li Guangpu et al: "The signal for translational readthrough of a UGA codon in sindbis virus RNA involves a single cytidine residue immediately downstream of the termination codon", Journal of Virology, Aug. 1993, vol. 67, No., 8 pp. 5062-6067.
McCaughan Kim K., et al: "Translational termination efficiency in mammals is influenced by the base following the stop codon", Proc. Natl. Acad. Sci. USA, vol. 92, Jun. 1995, pp. 5431-5435.
Brown Chris M., et al: "Sequence analysis suggests that tetranucleotides signal the termination of protein synthesis in eukaryotes", Nucleic Acids Research, vol. 18, No. 21, Oct. 9, 1990, pp. 6339-6345.
Bebbington C.R., et al: "High-level expression of a recombinant antibody from myeloma cells using a glutamine synthetase gene as an amplifiable selectable marker", Biotechnology, vol. 10, Feb. 1992, pp. 169-175.

(Continued)

*Primary Examiner* — Reza Ghafoorian
(74) *Attorney, Agent, or Firm* — Jason J. Derry

(57) ABSTRACT

The application describes a method of selecting mammalian host cells that express a polypeptide of interest with high yield. The host cells contain an expression cassette with a first polynucleotide encoding a polypeptide of interest, at least one leaky stop codon located downstream of the first polynucleotide and a second polynucleotide located downstream of the leaky codon encoding an immunoglobulin transmembrane anchor comprising a cytoplasmic domain. The host cells are cultivated to allow expression of the polypeptide of interest such that some of the polypeptides of interest are expressed as fusion proteins displayed on the cell surface. High producing cells are then selected based on the presence or amount of the displayed fusion polypeptides.

8 Claims, No Drawings

(56) References Cited

OTHER PUBLICATIONS

Hartman, Standish C., et al: "Two dominant-acting selectable markers for gene transfer studies in mammalian cells", Proc. Natl. Acad. Sci. USA, vol. 85, Nov. 1988, pp. 8047-8051.

Levitt N., et al: "Definition of an efficient synthetic poly(A) site", Genes & Development, vol. 3, 1989, pp. 1019-1029.

Subramani Suresh, et al: "Expression of the mouse dihydrofolate reductase comlementary deoxyribonucleic acid in simian virus 40 vectors", Molecular and Cellular Biology, Sep. 1981, pp. 854-864.

Eaton Dan L. et al: "Construction and characterization of an active factor VIII variant lacking the central one-third of the molecule", Biochemistry, vol. 25, No. 26, Dec. 30, 1986, pp. 8343-8347.

Neuberger Michael S.: "Expression and regulation of immunoglobulin heavy chain gene transfected into lymphoid cells", The EMBO Journal, vol. 2, No. 8, May 5, 1983, pp. 1373-1378.

Grillari Johannes, et al: "Analysis of alterations in gene expression after amplification of recombinant genes in CHO cells", Journal of Biotechnology, vol. 87, 2001 pp. 59-65.

Pack Peter, et al: "Tetravalent miniantibodies with high avidity assembling in *Escherichia coli*", Journal of Mol. Biol., vol. 246, pp. 28-34, 1995.

Pack Peter, et al: "Improved bivalent miniantibodies, with identical avidity as whole antibodies, produced by high cell density fermentation of *Escherichia coli*", Bio/Technology, vol. 11, No. 11, Nov. 1993, pp. 1271-1277.

Hust Michael, et al: "Single chain fab (scFab) fragment", BMC Biotechnology, vol. 7, No. 14, Mar. 8, 2007, pp. 1-15.

Oumard Andre, et al: "Recommended method for chromosome exploitation: RMCE-based cassette-exchange systems in animal cell biotechnology", Cytotechnology (2006), vol. 50, pp. 93-108.

Sorrell David A., et al: "Targeted modification of mammalian genomes", Biotechnology Advances, vol. 23 (2005), pp. 431-469.

Wurm Florian M.: "Production of recombinant protein therapeutics in cultivated mammalia", Nature Biotechnology, vol. 22, No. 11, Nov. 2004, pp. 1393-1398.

Pack Peter, et al: "Miniantibodies: use of amphipathic helices to produce functional, flexibly linked dimeric Fv fragments with high avidity in *Escherichia coli*", Biochemistry, vol. 31, No. 6, Feb. 18, 1992, pp. 1579-1584.

Achatz et al, The Open Immunology Journal 1:25-32, 2008.

Varriale et al, Molecular Phylogenetics and Evolution 57:1238-1244, 2010.

Manuvakhova et al, RNA 6:1044-1055, 2000.

B. Glick, Molecular Biotechnology, "Mir", 2002, Chapter 3, in Russian.

Bouquin et al, Journal of Biotechnology 125:516-528, 2006.

\* cited by examiner

CELL SURFACE DISPLAY OF POLYPEPTIDE ISOFORMS BY STOP CODON READTHROUGH

This is a National Stage of International Application No. PCT/EP2009/006246 filed on 28 Aug. 2009, which claims priority under 35 U.S.C. §119 to European Application Serial No. 08163161.6, filed 28 Aug. 2008, the entirety of each of which application is herein incorporated by reference.

The present invention pertains to a method for selecting high-producing mammalian host cells as well as to vectors and host cells suitable for use in a respective method. Furthermore, the present invention pertains to a method for efficiently producing polypeptides with a high yield.

Selection of high-producing cell lines is an important first step in the development of any bio-process and is one of the greatest challenges in biotechnology. One problem is that such high-producing clones are rare, may spend much of their energy on polypeptide production, and thus have reduced growth rates. This leads to overgrowth and non- or low producing-cells. However, in the production of polypeptides it is desirable to obtain cell lines producing the polypeptide of interest with a high yield. Traditionally, high-producing cell lines were selected by rounds of limiting dilution cloning followed by product analysis. However, this traditional route has several draw-backs as it is both labor intensive and costly. Beyond that, the whole process is time consuming and can take several months to complete and even then there is no guarantee that the clone cell line will be stable and so useful for industrial bioprocessing. Furthermore, selection of the highest producers can be compromised by practical limitations on the number of cells that can be screened thereby potentially reducing the efficiency of selection of low abundance, high productivity cells.

Therefore, there have been many efforts to provide alternative methods for selecting high producing clones. For example, flow cytometry has made it easier to monitor productivity and to isolate cells with specific characteristics. Important advantages of flow cytometry include the ability to screen large numbers of cells rapidly, with the capability to distinguish cell sub-populations and the ability to efficiently select low abundance cells demonstrating the desired characteristics. Most of the traditional approaches for selecting high productivity cells utilizing flow cytometry were established for the selection of hybridoma cells.

One approach is based on the cell surface antibody content of hybridoma cells displaying an increased amount of cell surface antibodies that can be identified and recovered through the use of fluorescence labeled antibodies. However, a quantitative correlation has not been broadly documented.

Further approaches were developed to select cells based on secreted antibody as an alternative strategy to circumvent some of the limitations of cells surface antibody selection. One approach applies an affinity matrix; the other uses a gel microdroplet technology. The former method is based on creation of an artificial affinity matrix, specific for the secreted product of interest. Secreted molecules bind to the affinity matrix on the surface of the secreting cell and are subsequently labeled with specific fluorescent reagents for flow cytometric analysis and cell sorting.

Microdroplet encapsulation involves complete encapsulation of single cells in agarose beads. These beads contain specific capture antibodies and so simultaneously capture secreted product and prevent cross feeding of product between cells.

Other methods rely on the co-expression of marker genes, which are detectable by flow cytometry. Disadvantages are a weak linkage of expression of the marker gene (for example green fluorescence protein) to the expression of the gene of interest. Furthermore, the expression of the marker gene costs cells additional energy and might induce stress.

An alternative method relies on an inducible co-expression of membrane bound capturing proteins. The membrane bound capturing proteins are anchored to the cell surface and capture the secreted polypeptide as soon as they are released from the cells. Those captured molecules can then be detected on the surface of the cell. However, genetically engineered host cells are necessary and also cross-feeding of non-producing cells might occur.

Also secreted products transiently associated to the cell membrane have been used in order to select producing cells. However, cross feeding of non-producing cells occurs and this method has a rather high background activity. Furthermore, it was found that it is not possible to perform several rounds of enrichment and selection.

Therefore, there is a need in developing a technology for selecting high-producing host cells. It is thus the object of the present invention to provide a method for detecting high producing recombinant host cells within a large populating of non-, low-, and/or medium-producing cells and to provide a method for producing polypeptides with a high yield.

The present invention solves this problem by providing a method for enriching or selecting at least one eukaryotic host cell expressing a desired level of a polypeptide of interest, comprising:

a) providing a plurality of eukaryotic host cells comprising a heterologous nucleic acid comprising at least one cassette (Cas-POI) comprising at least a first polynucleotide (Pn-POI) encoding the polypeptide of interest, at least one stop codon down-stream of the first polynucleotide, and a second polynucleotide downstream of the stop codon encoding an immunoglobulin transmembrane anchor or a functional variant thereof;

b) cultivating the eukaryotic host cells to allow expression of the polypeptide of interest such that at least a portion of the polypeptide of interest is expressed as a fusion polypeptide comprising the immunoglobulin transmembrane anchor or a functional variant thereof, wherein said fusion polypeptide is being displayed on the surface of said host cell;

c) selecting at least one eukaryotic host cell based upon the presence or amount of the fusion polypeptide displayed on the cell surface.

A "heterologous nucleic acid" refers to a polynucleotide sequence that has been introduced into a host cell e.g. by the use of recombinant techniques such as transfection. The host cell may or may not comprise an endogenous polynucleotide corresponding to, respectively being identical to the heterologous polynucleotide. However, in particular the term "heterologous nucleic acid" refers to a foreign polynucleotide introduced into the host cell. Introduction may be achieved e.g. by transfecting a suitable vector that may integrate into the genome of the host cell (stable transfection). In case the heterologous nucleic acid is not inserted into the genome, the heterologous nucleic acid can be lost at the later stage e.g. when the cells undergo mitosis (transient transfection). Both variants are suitable, however, stable transfection is preferred. Suitable vectors might also be maintained in the host cell without integrating into the genome, e.g. by episomal replication. However, also other techniques are known in the prior art for introducing a heterologous nucleic acid into a host cell which are also described in further detail below.

A "polynucleotide" is a polymer of nucleotides which are usually linked from one deoxyribose or ribose to another and refers to DNA as well as RNA, depending on the context. The term "polynucleotide" does not comprise any size restrictions.

A "cassette" describes a group of polynucleotide elements, operably linked to each other, comprising e.g. a polynucleotide (Pn-POI) encoding the polypeptide of interest, a polynucleotide encoding a immunoglobulin transmembrane anchor or a functional variant thereof, a polynucleotide encoding a marker, regulatory elements and/or other polynucleotides described herein. A "cassette" as used herein comprises at least two polynucleotide elements. A cassette may or may not comprise regulatory elements as polynucleotides such as e.g. a promoter, an enhancer and/or a polyA site. According to one embodiment, the cassette is an "expression cassette" suitable for expressing a polypeptide. An expression cassette comprises at least one transcription initiation element, e.g. a promoter, as regulatory element operably linked to a coding region, e.g. a polynucleotide (Pn-POI) encoding a polypeptide of interest, which is then accordingly under the transcriptional control of said transcription initiation element. An expression cassette may also comprise suitable regulatory elements for transcription termination, such as e.g. a polyA site.

The "cassette (Cas-POI)" comprises at least a first polynucleotide (Pn-POI) encoding the polypeptide of interest, at least one stop codon downstream of the first polynucleotide, and a second polynucleotide downstream of the stop codon encoding an immunoglobulin trans-membrane anchor or a functional variant thereof. Preferably, the cassette (Cas-POI) is an expression cassette (Exp-POI).

The "expression cassette (Exp-POI)" defines an expression cassette suitable for expressing a polypeptide of interest (POI). As expression cassette it comprises at least one transcription initiation element. Said expression cassette (Exp-POI) either comprises the polynucleotide (Pn-POI) encoding the polypeptide of interest as part of the coding region or comprises a site suitable for inserting a respective polynucleotide (Pn-POI) encoding the polypeptide of interest—depending on the used embodiment of the present invention which are described in further detail below.

The general concept of the present invention is to place a stop codon between the polynucleotide (Pn-POI) encoding the polypeptide of interest and the polynucleotide encoding the immunoglobulin transmembrane anchor or a functional variant thereof which allows anchoring of the polypeptide to the cell surface. The term "immunoglobulin transmembrane anchor" and "immunoglobulin transmembrane domain" are used as synonyms herein. The stop codon constitutes or is part of a translation termination signal and may be the natural stop codon of the polynucleotide encoding the polypeptide of interest and thus the stop codon that is naturally used to terminate translation. The design of the cassette (Cas-POI) results upon expression in the generation of two different polypeptides when the first and second polynucleotides are transcribed into a transcript, which is optionally processed, and subsequently translated. According to one translation variant, translation of the transcript is aborted at the (at least one) stop codon located between the polynucleotide (Pn-POI) encoding the polypeptide of interest and the polynucleotide encoding an immunoglobulin transmembrane anchor or a functional variant thereof. The termination of the translation at said stop codon results in a polypeptide product—not comprising the transmembrane anchor.

According to the second translation variant, translation reads through said at least one stop codon, thereby rendering a translation product comprising the polypeptide of interest and fused thereto the immunoglobulin transmembrane anchor or a functional variant thereof which is capable of anchoring the fusion polypeptide to the cell membrane. Such fusion polypeptide is transferred and fixed to the cell surface via the comprised immunoglobulin transmembrane anchor or functional fragment thereof. It is an important feature of the present invention that upon expression of the cassette (Cas-POI) the termination of the translation at said in frame stop codon is to a certain extent "leaky", as translational read-through occurs, thereby rendering the described fusion polypeptide. As this translational read-through occurs at a defined proportion—which can also be influenced by the choice and number of the stop codon(s) and the regions adjacent to the stop codon, in particular the nucleotide following the stop codon as well as by the culture conditions—the level of surface bound fusion polypeptide directly correlates with the expression level of the polypeptide of interest. The amount of fusion polypeptide present on the cell surface is thus to a certain extent proportional to the overall expression level of the polypeptide of interest by the respective cell, as there is a strong linkage between the surface expression of the fusion polypeptide and the productivity of the host cell in expressing the polypeptide of interest. The level of surface bound fusion polypeptide is therefore representative for the overall productivity of the individual cell and allows the selection of at least one eukaryotic host cell based upon the presence or amount of the fusion polypeptide displayed on the cell surface. A selection cycle comprising the steps a), b) and c) allows the efficient and reproducible identification and isolation of high producing eukaryotic host cells.

Suitable detection/selection methods like immunostaining, flow cytometry, fluorescent microscopy, MACS, affinity based methods such as magnetic beads and similar techniques allow the identification, selection and/or enrichment of high-producing cells based on the presence and level of surface bound fusion polypeptide. Therefore, the present invention leads to a drastic reduction in screening efforts by allowing the selection and also the enrichment of at least one high-producing cell or a population of high producing cells from a population of non-, low- and/or medium producing cells. It is also possible to perform several rounds of selection and/or enrichment, preferably two or three. E.g. a sufficient or even high expressing eukaryotic host cell or population of host cells may be selected by using a detection compound such as e.g. an antibody or fragment thereof recognizing the membrane anchored fusion polypeptide. Said detection compound may carry a label and can thus be detected by common detection methods.

According to the teachings of the present invention, at least a fragment of an immunoglobulin transmembrane anchor/domain is used in order to anchor the polypeptide of interest to the cell surface. In case a fragment instead of a full-length immunoglobulin transmembrane anchor is used, the respective fragment shall allow anchoring of the fusion polypeptide to the cell surface. The immunoglobulin transmembrane anchor/domain or functional fragment thereof is embedded in and thereby tightly anchored to the cell membrane. This tight anchorage distinguishes the anchors of the present invention from e.g. a GPI anchor. The immunoglobulin transmembrane anchor used according to the present invention provides a very robust and thus durable anchoring of the fusion polypeptide to the cell surface which is also not or at least less susceptible to proteolytic shedding.

This is confirmed by the performed product analysis after purification. No immunoglobulin transmembrane anchor (or immunoglobulin transmembrane anchor fragment) containing heavy chain species are found in the performed mass spectrometry analysis. This is an important advantage over the prior art as also the risk of contaminations of the secreted soluble polypeptide of interest by shedded fusion polypeptides is reduced. Furthermore, according to the analysed characteristics of the expressed polypeptides of interest, also no significant differences to material from conventional clones/expression systems are found.

Cells obtained by the method of the present invention have a higher average expression level than cells cloned by limited dilution or similar methods. They also have a higher average expression level than cells cloned for example by flow cytometry after transfection of a standard vector not comprising the specific transmembrane domain/anchor according to the present invention.

Cells that are identified as a result of the screening/selection procedure of the present invention will generally be isolated and may be enriched from non-selected cells of the original cell population. They can be isolated and cultured as individual cells. They can also be used in one or more additional rounds of selection, optionally for additional qualitative or quantitative analysis, or can be used e.g. in development of a cell line for protein production. According to one embodiment, an enriched population of high producing cells selected as described above is directly used as population for the production of the polypeptide of interest with high yield.

Advantageously, the observed growth behaviour and productivity of clones co-expressing the transmembrane variant of the polypeptide of interest, in particular antibodies and clones derived from a classical vector setup not co-expressing the transmembrane variant of the polypeptide of interest appear to be the same. Furthermore, also the clonal production stability appears to be equally good.

Also provided is a method for producing a polypeptide of interest with high yield, the method comprising:
  a) providing a plurality of eukaryotic host cells comprising a heterologous nucleic acid comprising at least one cassette (Cas-POI) comprising a first polynucleotide (Pn-POI) encoding the polypeptide of interest, at least one stop codon downstream of the first polynucleotide, and a second polynucleotide downstream of the stop codon encoding an immunoglobulin transmembrane anchor or a functional variant thereof;
  b) cultivating the eukaryotic host cells to allow expression of the polypeptide of interest such that at least a portion of the polypeptide of interest is expressed as a fusion polypeptide comprising the immunoglobulin transmembrane anchor or a functional variant thereof, wherein said fusion polypeptide is being displayed on the surface of said host cell;
  c) selecting at least one eukaryotic host cell based upon to the presence or amount of the fusion polypeptide displayed on the cell surface;
  d) culturing the selected eukaryotic host cell in culture medium under conditions that allow for expression of the polypeptide of interest.

The expressed polypeptide of interest may be obtained by disrupting the host cells. The polypeptides may also be expressed, e.g. secreted into the culture medium and can be obtained therefrom. Also combinations of the respective method are possible. Thereby, polypeptides can be produced and obtained/isolated efficiently with high yield. The obtained polypeptides may also be subject to further processing steps such as e.g. purification and/or modification steps in order to produce the polypeptide of interest in the desired quality. According to one embodiment, said host cells are cultured under serum-free conditions. As is outlined above, by inserting at least one stop codon between the polynucleotide (Pn-POI) encoding the polypeptide of interest and the second polynucleotide encoding an immunoglobulin transmembrane anchor or functional fragment thereof, the selection of high expressing host cells is possible, thereby allowing the production of the polypeptide of interest with high yield. The selection/enrichment step of the present invention is thus an integral and important component of the overall production process.

The use of an immunoglobulin transmembrane anchor or functional fragment thereof according to the teachings of the present invention is particularly advantageous when producing immunoglobulin molecules, as said immunoglobulin transmembrane anchor is naturally suitable to fix immunoglobulin molecules to the cell surface. Surprisingly, it is found that the immunoglobulin transmembrane anchor can be used when expressing immunoglobulin molecules in mammalian host cells such as CHO cells. This is surprising, as the prior art assumed that the co-expression of the Ig alpha and Ig beta receptor chains is necessary in said cells in order to achieve surface—and accordingly cell membrane anchored—expression of antibodies when using the Ig transmembrane domain as anchor. These co-receptors are e.g. naturally expressed in B-cells and B-cell derivatives such as hybridoma or myeloma cells (e.g. SP2/0 cells) but are not expected to be expressed in non B-cells such as CHO cells. However, it is found that despite the missing expression of the co-receptors the surface display of the polypeptides of interest and in particular of immunoglobulin molecules worked well on non B-cell derivatives such as CHO cells when using the Ig transmembrane anchor/domain. Hence, according to one embodiment a eukaryotic host cell is used which is not a B-cell or a B-cell derivative. Accordingly, a eukaryotic, preferably a mammalian host cell used which does not naturally express the Ig alpha and Ig beta receptor chains. Thus, preferably, the host cell is a CHO cell. Furthermore, according to one embodiment, no artificial co-expression of the Ig alpha and Ig beta receptor chain occurs in said eukaryotic host cell.

Any immunoglobulin transmembrane anchor or functional fragment thereof can be used according to the teachings of the present invention. In particular, the immunoglobulin trans-membrane anchor is selected from the group consisting of immunoglobulin transmembrane anchors derived from IgM, IgA, IgE, IgG and/or IgD or functional variants thereof. Preferably, the immunoglobulin transmembrane anchor is derived from IgG1, IgG2, IgG3 and/or IgG4. Particularly suitable is an IgG1 immunoglobulin transmembrane anchor or a functional variant thereof. Preferred examples of an IgG derived transmembrane anchor are shown in SEQ ID NO: 2 and SEQ ID NO: 7.

According to one embodiment, the immunoglobulin transmembrane anchor comprises a cytoplasmatic domain. The use of an immunoglobulin transmembrane anchor comprising a cytoplasmatic domain is preferred as it provides a very tight anchorage of the fusion polypeptide to the cell surface. Particularly suitable is the use of an immunoglobulin cytoplasmatic domain. According to one embodiment, the immunoglobulin cytoplasmatic domain is derived from IgG, IgA and IgE or functional variants of the foregoing. These immunoglobulin cytoplasmatic domains are larger than the ones derived from IgD and IgM. SEQ ID NO: 4 and SEQ ID NO: 6 show suitable amino acid sequences of IgG derived cytoplasmatic domains that can be used as cytoplasmatic domain. A preferred example of an IgG derived trans-membrane anchor which comprises an IgG derived cytoplasmatic domain is shown in SEQ ID NO: 3.

Thus, the immunoglobulin transmembrane anchor may comprise a polypeptide sequence as shown in SEQ ID NO: 2 and/or SEQ ID NO: 3 or functional variants, in particular functional fragments thereof, which allow the anchoring of the fusion polypeptide to the surface of the host cell.

The nucleotide sequence of a section of a suitable cassette (Cas-POI) is shown as SEQ ID NO:1. The shown detail comprises an in frame stop codon suitable for translational read through and a polynucleotide encoding a particularly suitable immunoglobulin (Ig) transmembrane domain that can be used according to the teachings of the present invention. The stop codon is located in frame downstream of the polynucleotide encoding the polypeptide of interest and thus the polynucleotide sequence that is transcribed and processed into an amino acid sequence. The coding sequence refers to the sequence that is translated into amino acids. Thus, the stop codon does not belong to the coding sequence and accordingly to the polynucleotide encoding the polypeptide of interest. The stop codon can be the natural stop codon of the polynucleotide encoding the polypeptide of interest. In this case, no additional stop codon(s) need(s) to be but may be present (see above).

The second polynucleotide of the cassette (Cas-POI) may encode an immunoglobulin trans-membrane anchor or a functional variant thereof, which comprises a polypeptide sequence shown as SEQ ID NO: 2. SEQ ID NO: 3 shows a further variant of a suitable immunoglobulin transmembrane domain, also comprising a cytoplasmatic domain (the cytoplasmatic domain alone is also shown as SEQ ID NO: 4), the putative amino acids corresponding to the leaky stop codon and the additional codon (WL) and a connecting region (the connecting region alone is also shown as SEQ ID NO: 5). Also other amino acids can be present in the position corresponding to the at least one stop codon and the adjacent codon, depending on the chosen stop codon and/or number of stop codons and the used adjacent codon(s). As these amino acids are only present in the fusion polypeptide, they do not alter the amino acid sequence of the polypeptide of interest. Accordingly, an immunoglobulin transmembrane domain comprising a polypeptide sequence as shown as SEQ ID NO: 2 or 3 or a functional variant, in particular a functional fragment thereof can be used as a transmembrane anchor according to the teachings of the present invention and hence in the described methods, as well as in the described vectors and host cells.

"A functional variant" of an immunoglobulin transmembrane anchor according to the present invention include immunoglobulin transmembrane anchors having one or more amino acid sequence exchanges (e.g. deletions, substitutions or additions) with respect to the amino acid sequence of the respective natural immunoglobulin transmembrane domain and functional fragments of the foregoing, which allow transmembrane anchoring of the fusion polypeptide to the cell surface.

As translation termination signal and thus stop codon any one of the three stop codons that signal termination of protein synthesis (TAA (UAA), TAG (UAG) and TGA (UGA)—also in various tetranucleotide contexts, see below) can be used between the polynucleotide (Pn-POI) encoding the polypeptide of interest and the polynucleotide encoding the immunoglobulin transmembrane anchor or a functional variant thereof, depending on the desired level of suppression (read-through). As is outlined above, the stop codon may also be the natural stop codon of the polynucleotide encoding the polypeptide of interest. Preferably, said translation termination signal has an incomplete termination efficiency in order to promote translational read through. The "leakyness" of the stop codon is also influenced by the codon(s) adjacent and thus downstream of the at least one stop codon, in particular the first nucleotide may influence the transcriptional read-through (see below).

The cassette (Cas-POI) needs to be transcribed in order to allow the expression of the polypeptide of interest. According to one embodiment, the cassette (Cas-POI) is therefore an expression cassette. According to a further embodiment, the cassette (Cas-POI) is integrated into the genome of the host cell such that the cassette (Cas-POI) is under the transcriptional control of a transcription initiation element of the host cell, such as an promoter.

Transcription of the nucleic acid comprised in the cassette (Cas-POI) results in a transcript comprising at least
- a first polynucleotide, wherein translation of said first polynucleotide results in the polypeptide of interest;
- at least one stop codon downstream of said first polynucleotide;
- a second polynucleotide downstream of said stop codon, wherein translation of said second polynucleotide results in the immunoglobulin transmembrane anchor or a functional variant thereof.

At least a portion of the transcript is translated into a fusion polypeptide comprising the polypeptide of interest and the immunoglobulin transmembrane anchor or a functional variant thereof by translational read-through of the at least one stop codon. Translational read-through may occur naturally due to the choice of the stop codon/design of the translation termination signal or can be induced by adapting the culturing conditions, e.g. by using a termination suppression agent (see below).

The cassette (Cas-POI) used in the method of the invention may comprise only a single stop codon upstream of the coding sequence for the immunoglobulin transmembrane anchor or fragment thereof. However, it is also possible to use a series of two or more stop codons, e.g. two or three, or four stop codons, which may be the same or different. Also the context of the stop codon, i.e. the trinucleotide stop codon itself as well as the nucleotide(s) respectively codon immediately downstream of the stop codon, has an influence on the read-through levels. However, it needs to be ensured that a certain level of translational read-through still occurs in order to allow the production of the fusion polypeptide which may be achieved according to one embodiment by adjusting the culture conditions.

The primary transcript may be a pre-mRNA comprising introns. A respective pre-mRNA would be processed (spliced) into mRNA. Alternatively, transcription may result directly in mRNA. During translation of the mRNA transcript there is usually a natural level of background read-through of the stop codon(s) or a respective read-through level can be induced by adapting the culture conditions. This read-through level results in a certain proportion of fusion polypeptides that also depends on the number and nature of the used stop codon(s), the downstream stop codon and in particular the tetranucleotide context of the stop codon(s) and the culture conditions. Accordingly, a certain proportion of fusion polypeptide is produced according to the teachings of the present invention despite the presence of the stop codon. These fusion polypeptides comprise the immunoglobulin transmembrane anchor or a functional variant thereof, tightly anchoring the fusion polypeptides to the cell surface. As a result, the fusion polypeptides are displayed at the surface of the host cells, and cells displaying high levels of membrane-anchored recombinant fusion polypeptides (indicating a high level of secreted polypeptide) can be selected e.g. by flow cytometry, in particular by fluorescence activated cell sorting (FACS) when contacted with an appropriately labelled detection compound.

Suitable translation termination signals and thus stop codons and stop codon settings with incomplete translation termination efficiency can be designed as described in the prior art (see e.g. Li et al. 1993, Journal of Virology 67 (8), 5062-5067; McCughan et al. 1995 Proc. Natl. Acad. Sci. 92, 5431-5435; Brown et al 1990, Nucleic Acids Research 18 (21) 6339-6345, herein incorporated by reference).

According to one embodiment, the following stop codon setting is used; the stop codon is shown in bold and underlined:

TGACTA nucleotide sequence of the stop coding setting on the coding strand and thus on the DNA level; the stop codon is shown in bold and underlined UGACUA nucleotide sequence of the stop codon setting on the RNA level W L putative amino acids corresponding to the stop codon and the adjacent codon if translational read-through occurs; shown is thus the most likely read-through product of the shown polynucleotide The additional amino acids that are incorporated into the fusion polypeptide due to the read-through of the stop codon can be of any kind as long as the fusion protein is displayed on the cell surface. As said additional amino acids are only incorporated into the fusion polypeptide, the amino acid of the polypeptide of interest remains unaltered.

In addition to the possible use of multiple stop codons following the polynucleotide (Pn-POI) encoding the polypeptide of interest, it will normally be advantageous to use multiple stop codons downstream of the sequence encoding the immunoglobulin transmembrane anchor or functional fragment thereof. The use of multiple stop codons in this position, e.g. up to about ten stop codons, such up to about six or eight stop codons, such as about two, three, four or five stop codons, will ensure efficient termination of translation.

The amount of fusion polypeptide present and thus detectable on the cell surface usually increases during polypeptide synthesis as the fusion polypeptide remains anchored to the cell membrane and thus accumulates on the cell surface as expression continues. According to one embodiment, the cassette (Cas-POI) is constructed such that stop codon read-through results in approximately ≤50%, ≤25%, ≤15%, ≤10%, ≤5%, ≤2.5%, ≤1.5%, ≤1% or less than ≤0.5% fusion polypeptide. The remaining portion is produced as the polypeptide form not comprising the immunoglobulin transmembrane anchor or functional fragment thereof. As described, the level of stop codon read through can be influenced by the choice and number of the stop codon(s) and the regions adjacent to the stop codon, in particular the nucleotide following the stop codon, as well as by the culture conditions used during step b).

Depending on factors such as the natural level of background read-through for a given stop codon in a given construct, it may in some cases be desirable to use more than one stop codon between the polynucleotide (Pn-POI) encoding the polypeptide of interest and the polynucleotide encoding the immunoglobulin transmembrane anchor in order to further reduce background read-through levels (see above). The general advantage of a rather low read-through level is a higher stringency in the subsequent selection/enrichment and sorting procedure, which is preferably done by FACS, leading to a better resolution of high producing versus ultra high producing clones. If read-through levels are too high, saturation of the cell surface capacity for membrane bound polypeptides might occur, which may prevent discrimination of expression levels, in particular of high expression levels. Therefore, a rather low read-through level is advantageous in order to select ultra high expressing clones. Accordingly, preferably only ≤5%, ≤2% or even ≤1.5% of the transcript is translated into a fusion polypeptide.

However, it is also possible to increase the read-through level if necessary/desired, e.g. by using a termination suppression agent during culturing. The use of a termination suppression agent in the culture media during step b) is one way of influencing the level of stop codon read through by the culture conditions. A termination suppression agent is a chemical agent which is able to suppress translational termination resulting from the presence of a stop codon. In particular, the termination suppression agent is an antibiotic belonging to the aminoglycoside group. Aminoglycoside antibiotics are known for their ability to allow insertion of alternative amino acids at the site of a stop codon, thereby resulting in "read-through" of a stop codon or stop codon setting that otherwise normally would result in translation termination. Aminoglycoside antibiotics include G-418, gentamycin, paromomycin, hygromycin, amikacin, kanamycin, neomycin, netilmicin, streptomycin and tobramycin. However, as a low read-through level is advantageous, selection is preferably performed in the absence of a termination suppression agent.

The present invention is applicable to any type of host cell in which translational stop codon read-through occurs at least to a small percentage or can be induced by the addition of a termination suppression agent. Examples of suitable eukaryotic host cells are mammalian hosts cells which include e.g. Chinese hamster ovary (CHO) cell lines, green monkey cell lines (COS), mouse cells (for example NS/0), baby hamster kidney (BHK) cell lines and human cells and cell lines. Preferably, the host cell is a CHO cell line.

While one selection cycle is sufficient to identify good producing host cells, according to one embodiment, two or more selection cycles are performed, wherein in each selection cycle at least one eukaryotic host cell is selected based upon the presence or amount of the fusion polypeptide displayed on the cell surface. The experimental results demonstrate that a second selection cycle usually leads to improved results.

According to one embodiment, the selection step c) comprises contacting the plurality of host cells with a detection compound binding the fusion polypeptide and selecting at least one host cell based upon the presence or amount of the detection compound bound to the cell surface.

The detection compound used for binding to the fusion polypeptide may have at least one of the following characteristics:

said compound is labelled;
said compound is fluorescently labelled;
said compound is an antigen;
said compound is an immunoglobulin molecule or a binding fragment thereof;
said compound is protein-A, -G, and/or -L.

The detection compound used for binding the fusion polypeptide at the cell surface can for example be an immunoglobulin molecule or a fragment thereof such as an antibody or antibody fragment, recognising the fusion polypeptide. Basically all accessible portions of the fusion polypeptide can be detected, thereunder also the portion corresponding to the polypeptide of interest which is secreted in parallel to the fusion polypeptide in soluble form.

According to one embodiment, the detection compound is an antigen. This embodiment is suitable, if the expressed polypeptide of interest is for example immunoglobulin molecule or a fragment thereof such as an antibody, binding the respective antigen.

In order to allow detection and selection, said detection compound used for binding the fusion polypeptide may be labelled. The labelled detection compound that binds the fusion polypeptide displayed on the cell surface thereby labels respectively stains the cell surface. The higher the amount of fusion polypeptide that is expressed by the host cell, the more labelled detection compound is bound. This has the advantage that the selection of the host cells can be easily performed as not only the presence but also the amount of the bound detection compound can be determined due to the label. To select high producing host cells, those host cells are selected from the population of host cell which are most effectively respectively intensively labelled by the detection compound. A fluorescent label is preferred as this allows easy detection by fluorescence detecting methods such as for example flow cytometry. Suitable fluorescent labels are known to the skilled person.

According to one embodiment, one or more selection cycles, preferably two or three, may be performed to select at least one eukaryotic host cell based on the degree of binding of the detection compound to the cell surface. According to this embodiment, at least one eukaryotic host cell is selected in each selection cycle based upon the amount of bound detection compound. Thus, those host cells that were most effectively/intensively labelled are selected based upon the degree respectively amount of cell surface staining. E.g. the top 5% or the top 2% of the host cells can be selected.

In case several eukaryotic host cells are supposed to be selected together as a pool (so called pool enrichment), several cells, e.g. at least 10, at least 50, at least 500, at least 1000 or at least 50.000 are selected and included in a cell pool. This embodiment is particularly advantageous for quickly obtaining larger amounts of the polypeptide of interest as the cell pool comprising several high producing host cells selected according to the teachings of the present invention can be expanded more quickly than e.g. a cell clone.

Thus, besides the application for selective cell cloning, the present invention can also be used for pool enrichment of high-producing cells whereby titers comparable to clonal cell lines can be achieved.

High-producing host cells can be isolated and/or a population of high producing cells can be enriched based on the degree of binding of the detection compound to the cell surface, in particular the fusion polypeptide. Binding of the detection compound to the fusion polypeptide on the surface of the host cell can be detected by flow cytometry, preferably fluorescence activated cell sorting (FACS).

In a preferred embodiment, host cells comprising a high amount of fusion polypeptides which accordingly depict a high signal are sorted using fluorescence-activated cell sorting (FACS). In the context of the present invention, FACS sorting is particularly advantageous, since it allows rapid screening of large numbers of host cells to identify and enrich those cells which express the polypeptide of interest with a high yield. As according to the preferred embodiment approximately only 5% or less of the polypeptide are produced as a fusion polypeptide, a higher fluorescence detected on the cell surface would correspond to a higher expression also of the polypeptide of interest, which can be e.g. secreted into the culture medium. Those cells, showing the highest fluorescence rate can be identified and isolated by FACS. A positive and statistically significant correlation between fluorescence, as determined by FACS and the amount of produced polypeptide is found and confirmed by the examples. Therefore, FACS sorting can be used not only for a qualitative analysis to identify cells expressing a polypeptide of interest in general, but can actually be used quantitatively to identify those host cells that express high levels of the polypeptide of interest. Therefore, high-producing host cells can be selected/enriched based on the degree of binding of the labelled detection compound to the fusion polypeptide, which is anchored to the cell surface. Thereby the best producing cells can be selected/enriched. The experimental results show that using the selection procedure according to the present invention in combination with FACS analysis led to a significant reduction of non-producing clones in the selected cell populations. Furthermore, the highly increased average productivity of the clones allows the drastic reduction of clone screening efforts e.g. in the cell line development process for biopharmaceutical production. Thus, cell lines for a much higher number of candidates or projects can be developed with less resources compared to classical screening approaches. Also, this process allows the evaluation of the productivity potential and clonal distribution of transfected and selected pools by surface staining and FACS analysis instead of time consuming productivity assays. Surface staining may also be used to analyze the clonal production stability with regards to the homogeneity of the cell population. Non- or low-producing sub-populations that may arise would be easily detectable.

According to one embodiment, the cassette (Cas-POI) and/or (Cas-POI') further comprises
  a polynucleotide (Pn-TAG) encoding an affinity tag located downstream of the at least one stop codon which is located downstream of the first polynucleotide and wherein said polynucleotide (Pn-TAG) is located upstream of the second polynucleotide encoding an immunoglobulin transmembrane anchor or a functional variant thereof and/or
  a polynucleotide (Pn-MARKER) encoding a selectable marker.

To provide the polynucleotide (Pn-TAG) as defined above between the stop codon and the polynucleotide encoding the immunoglobulin transmembrane anchor has the advantage that an affinity tag is incorporated into the fusion protein. As the affinity tag is located downstream of the at least one stop codon, it is only included in the fusion variant of the polypeptide of interest. An "affinity tag" refers to a short amino acid sequence which can be detected/bound by binding compounds/agents such as antibodies. Basically, the affinity tag serves as a target for capture agents and/or detection compounds. As it is located between the polypeptide of interest and the immunoglobulin transmembrane anchor or a functional variant thereof, it is also displayed on the cell surface and is accordingly accessible e.g. for detection compounds. The affinity tag may thus also function as target for the detection compound in order to allow the selection of suitable eukaryotic host cells. To use e.g. a well characterised affinity tag as target for detection/selection is advantageous as existing and well characterised detection compounds may be used for detection. Furthermore, the same detection compound can be used for different kinds of polypeptides of interest to be expressed. The generation of detection compounds specific for the different polypeptide of interest would be obsolete according to this embodiment as the same detection compound specific for the affinity tag could be used. As the affinity tag constitutes an integral part of the fusion polypeptide it is also tightly anchored to the surface of the eukaryotic host cell due to the presence of the transmembrane anchor. The tightly anchored fusion polypeptides should not be susceptible to shedding (see above).

Shedding of membrane bound fusion proteins may constitute—depending on the intended use of the secreted polypeptide—a contamination problem even if shedding is a rare event when using an immunoglobulin transmembrane anchor. E.g. when expressing therapeutic polypeptides/proteins, it is desirable to obtain the secreted product as pure as possible. When using an affinity tag such as e.g. a His tag, said affinity tag would be at least partially comprised in the shedded protein. Due to the presence of the affinity tag it is possible to remove shedded fusion polypeptides (if present) from the sample of secreted polypeptides by using conventional affinity purification procedures (e.g. Ni-NTA in case of a His tag). The affinity tag is therefore useful in order to easily remove potential contaminations from the sample.

Furthermore, the affinity tag can be used in order to control the purity of the expressed/obtained polypeptide. For applications where highly pure proteins/polypeptides are needed it may also be advantageous/mandatory to provide suitable assays to demonstrate that the product obtained is pure and accordingly does not comprise contaminations due to shedded fusion polypeptides. Such an assay could be based on the detection of the affinity tag. As the affinity tag is only present in the fusion polypeptide, it may serve as a specific marker for the presence of fusion polypeptides (or degraded/shedded versions thereof) in the sample. If the affinity tag can still be detected in the obtained product when using a detection compound specific for the affinity tag, there are still traces of shedded fusion polypeptide in the sample and the sample may need—depending on the amount—further purification. If no affinity tag can be detected in the sample, no or respectively very low amounts of shedded fusion polypeptide should be present in the analysed sample thereby ensuring that the sample is sufficiently pure for the intended application.

Accordingly, when producing the polypeptide of interest, the obtained polypeptide of interest can be further processed by
- removing contaminations of shedded fusion polypeptide by affinity purification targeting the affinity tag and/or
- detecting the presence or absence of shedded fusion protein by targeting the affinity tag.

Suitable examples for affinity tags are e.g. V5, a His Tag, FLAG, Strep, HA, c-Myc or the like. Suitable affinity tags can also be artificially created.

According to a further embodiment, the cassette (Cas-POI) and/or (Cas-POI') comprises a further polynucleotide (Pn-MARKER) encoding a selectable marker. Preferably, said selectable marker is located downstream of the polynucleotide encoding the immunoglobulin transmembrane anchor and is thus upon expression of the construct located on the cytoplasmatic site of the cell membrane when the fusion polypeptide is displayed. According to one embodiment, no stop codon is located between the polynucleotide encoding the immunoglobulin transmembrane anchor/domain or a functional variant thereof and the polynucleotide (Pn-MARKER), as they are supposed to be expressed as a fusion. Suitable stop codons and transcription termination signals should be provided downstream of the coding sequence of the polynucleotide (Pn-MARKER) to ensure efficient transcription and translation termination after expression of the polynucleotide (Pn-MARKER). Said polynucleotide (Pn-MARKER) can e.g. be a drug resistance gene or a reporter gene. Suitable examples are described herein. According to one embodiment, green fluorescence protein (GFP) or luciferase is used as reporter. This allows the selection of the eukaryotic host cells based upon two fusion protein characteristics.

According to one embodiment, the cassette (Cas-POI) and/or (Cas-POI') is an expression cassette. Persons skilled in the art will be capable of selecting suitable vectors, expression control sequences and hosts for performing the methods of the invention. For example, in selecting a vector, the host must be considered because the vector may need to be able to replicate in it and/or be able to integrate into the chromosome. Suitable vectors that can be used in the selection and production methods according to the present invention are also described below and in the claims.

Also a vector nucleic acid suitable for expressing at least one polypeptide of interest in a eukaryotic, preferably a mammalian host cell is provided, comprising at least one cassette (Cas-POI) comprising an insertion site for a first polynucleotide (Pn-POI) encoding the polypeptide of interest and/or a first polynucleotide (Pn-POI) encoding a polypeptide of interest, at least one stop codon downstream of the first polynucleotide, and a second polynucleotide downstream of the stop codon encoding an immunoglobulin transmembrane anchor or a functional variant thereof.

A "vector nucleic acid" according to the present invention is a polynucleotide capable of carrying at least one foreign nucleic acid fragment. A vector nucleic acid functions like a "molecular carrier", delivering fragments of nucleic acids into a host cell. It may comprise at least one expression cassette comprising regulatory sequences. Preferably, the vector nucleic acid comprises at least one expression cassette. Foreign polynucleotides may be inserted into the expression cassette(s) of the vector nucleic acid in order to be expressed therefrom. The vector nucleic acid according to the present invention may be present in circular or linearized form. The term "vector nucleic acid" also comprises artificial chromosomes or similar respective polynucleotides allowing the transfer of foreign nucleic acid fragments.

A respective vector can be used as expression vector in order to perform the screening and production methods described above. The advantages of a respective vector nucleic acid are also described above in conjunction with the screening method.

Said vector nucleic acid may further comprise at least
- a first polynucleotide (Pn-POI) encoding the polypeptide of interest;
- an expression cassette (Exp-MSM) comprising a mammalian selectable marker gene; and/or
- an expression cassette (Exp-MASM) comprising a mammalian amplifiable, selectable marker gene.

The expression cassette (Exp-MSM) defines the expression cassette comprising a <u>m</u>ammalian <u>s</u>electable <u>m</u>arker gene.

The expression cassette (Exp-MASM) defines the expression cassette comprising a <u>m</u>ammalian <u>a</u>mplifiable, <u>s</u>electable <u>m</u>arker gene.

The terms "5'" and "3'" is a convention used to describe features of a nucleic acid sequence related to either the position of genetic elements and/or the direction of events (5' to 3'), such as e.g. transcription by RNA polymerase or translation by the ribosome which proceeds in 5' to 3' direction. Synonyms are upstream (5') and downstream (3'). Conventionally, DNA sequences, gene maps, vector cards and RNA sequences are drawn with 5' to 3' from left to right or the 5' to 3' direction is indicated with arrows, wherein the arrowhead points in the 3' direction. Accordingly, 5' (upstream) indicates genetic elements positioned towards the left hand side, and 3' (downstream) indicates genetic elements positioned towards the right hand side, when following this convention.

The arrangement and orientation of the expression cassettes is also an important aspect. According to one embodiment, the expression cassette (Exp-MASM) is located 5' and the expression cassette (Exp-MSM) is located 3' of the expression cassette (Exp-POI). Further expression cassettes may be inserted between the expression cassettes (Exp-POI) and (Exp-MSM), such as e.g. an additional expression cassette (Exp-POI') for expressing an additional polypeptide of interest (described in further detail below). The expression cassettes (Exp-MASM), (Exp-POI) and (Exp-MSM) are preferably all arranged in the same 5' to 3' orientation. The inventors found, that this particular vector nucleic acid configuration allows the fast generation of high yielding cell lines.

According to one alternative, the expression cassette (Exp-POI) does not comprise the polynucleotide (Pn-POI) encoding the polypeptide of interest. Thus, an "empty" expression vector with an expression cassette (Exp-POI) is provided which does not yet comprise the polynucleotide (Pn-POI) encoding the polypeptide of interest. However, said polynucleotide (Pn-POI) encoding the polypeptide of interest can be incorporated into the expression cassette (Exp-POI) by using appropriate cloning methods, for example by using restriction enzymes in order to insert the polynucleotide (Pn-POI) encoding the polypeptide of interest into the expression cassette (Exp-POI). For this purpose the expression cassette (Exp-POI) may comprise e.g. a multiple cloning site (MCS) which can e.g. be used in all reading frames. A respective "empty" vector nucleic acid can e.g. be provided to customers, which then insert their specific polynucleotide of interest into the expression cassette (Exp-POI). The polynucleotide (Pn-POI) encoding the polypeptide of interest is inserted such that a stop codon is present between the polynucleotide (Pn-POI) encoding the polypeptide of interest and the polynucleotide encoding the transmembrane anchor or a functional variant thereof. The expression cassette (Exp-POI) may also comprise a replacement polynucleotide or a stuffer nucleic acid sequence, which can be excised and replaced by the polynucleotide (Pn-POI) encoding the polypeptide of interest. The present invention also provides a vector nucleic acid as described above, comprising an expression cassette (Exp-POI) comprising a first polynucleotide (Pn-POI) encoding the polypeptide of interest, at least one stop codon down-stream of the first polynucleotide, and a second polynucleotide downstream of the stop codon encoding an immunoglobulin transmembrane anchor or a functional variant thereof. This embodiment pertains basically to the final expression vector nucleic acid. Basically the same applies in case a cassette (Cas-POI) is used instead of an expression cassette (Exp-POI).

According to one embodiment, the vector nucleic acid is circular and the expression cassette (Exp-MSM) is arranged 3' of the expression cassette (Exp-POI) and the expression cassette (Exp-MASM) is arranged 3' of the expression cassette (Exp-MSM).

The expression vector according to the present invention may comprise an additional expression cassette (Exp-POI') for expressing a polypeptide of interest. In the final vector nucleic acid, said additional expression cassette (Exp-POI') comprises the additional polynucleotide for expressing the additional polypeptide of interest. Depending on the polypeptides to be expressed, said additional expression cassette (Exp-POI') may or may not comprise a polynucleotide encoding a membrane anchor (or a signal peptide for attaching a respective anchor, such as a GPI anchor), which is separated from the polynucleotide encoding the additional polypeptide of interest by a stop codon. Therefore, it is also possible that several expression cassettes for expressing different polypeptides are arranged in the expression vector according to the present invention. However, only the expression cassette (Exp-POI) needs to have the leaky stop codon assembly and thus a stop codon downstream of the first polynucleotide (Pn-POI) encoding the polypeptide of interest and a second polynucleotide downstream of the stop codon encoding an immunoglobulin transmembrane anchor or a functional variant thereof, the additional expression cassettes (Exp-POI') may or may not have a respective stop codon assembly.

A respective embodiment using at least two expression cassettes (Exp-POI) and (Exp-POI') for expressing the polypeptides of interest is particularly advantageous, in case an immunoglobulin molecule or functional fragment thereof is expressed. Accordingly, a vector nucleic acid for expressing at least one immunoglobulin molecule or a functional fragment thereof is provided, comprising an expression cassette (Exp-POI) comprising a first polynucleotide encoding the heavy and/or the light chain of the immunoglobulin molecule or a functional fragment thereof, at least one stop codon downstream of the first polynucleotide, and a second polynucleotide downstream of the stop codon encoding at least an immunoglobulin transmembrane anchor or functional fragment thereof; and/or an additional expression cassette (Exp-POI') comprising a polynucleotide encoding the corresponding light and/or the heavy chain of an immunoglobulin molecule or a functional fragment thereof. The expression cassette (Exp-POI') encodes the immunoglobulin chain that corresponds to the immunoglobulin chain of the expression cassette (Exp-POI) (i.e. if the expression cassette (Exp-POI) encodes the heavy chain, the expression cassette (Exp-POI') encodes the light chain and vice versa). Thus, a functional immunoglobulin molecule (or fragment thereof) can be expressed from the vector.

It is preferred that the heavy chain or a functional fragment thereof is expressed from the expression cassette (Exp-POI) and is thus according to a certain extent expressed as a fusion polypeptide. The corresponding light chain or a functional fragment thereof is according to one embodiment expressed from an expression cassette (Exp-POI'). Said expression cassette (Exp-POI') may be located on the same vector nucleic acid. However, it may also be located on a separate vector nucleic acid. However, it is preferred that the expression cassettes (Exp-POI) and (Exp-POI') are located on one vector nucleic acid. It is also possible to express both chains (the heavy chain and the corresponding light chain) from one expression cassette. E.g. they may be expressed as a fusion polypeptide comprising a self-splicing signal or a protease susceptible site in order to obtain two separate chains. Also possible is a bi- or multicistronic set up, wherein two or more polypeptides (POI and POI') are obtained from one mRNA which may comprise e.g. one or more internal ribosomal entry sites.

According to one embodiment, a vector nucleic acid for expressing at least one immunoglobulin molecule or a functional fragment thereof is provided, comprising an expression cassette (Exp-POI) comprising a first polynucleotide encoding the heavy chain of an immunoglobulin molecule or a functional fragment thereof, at least one stop codon downstream of the first polynucleotide, and a second polynucleotide downstream of the stop codon encoding an immunoglobulin transmembrane anchor or a functional variant thereof; and an additional expression cassette (Exp-POI') comprising a polynucleotide encoding the corresponding light chain of an immunoglobulin molecule or a functional fragment thereof.

Preferably, the expression cassette (Exp-POI) comprises the heavy chain and both expression cassettes (Exp-POI) and (Exp-POI') are arranged in the same orientation. Preferably, the expression cassette (Exp-POI') is arranged 5' of the expression cassette (Exp-POI). To arrange the expression cassette for the light chain 5' to the expression cassette of the heavy chain proved to be beneficial regarding the expression rate of immunoglobulin molecules. According to one embodiment, it is also destined to design the expression vector such, that the expression cassette(s) already comprise the immunoglobulin transmembrane anchor and the at least one leaky stop codon (e.g. comprised in a stuffer sequence) and, optionally, at least part of the constant regions of an immunoglobulin molecule. The fragments encoding the variable parts of the immunoglobulin molecules can then be inserted by the user/customer into the expression cassettes by using appropriate cloning strategies in order to obtain the final expression vector.

Non-limiting examples for mammalian selectable marker genes that can be comprised in the expression cassette (Exp-MSM) include antibiotic resistance genes e.g. conferring resistance to G418; hygromycin (hyg or hph, commercially available from Life Technologies, Inc. Gaithesboro, Md.); neomycin (neo, commercially available from Life Technologies, Inc. Gaithesboro, Md.); zeocin (Sh Ble, commercially available from Pharmingen, San Diego Calif.); puromycin (pac, puromycin-N-acetyl-transferase, available from Clontech, Palo Alto Calif.), ouabain (oua, available from Pharmingen) and blasticidin (available from Invitrogen). Said mammalian selectable marker genes allow the selection of mammalian host cells comprising said genes and thus of host cells comprising the vector. The term "gene" as used herein not only refers to the coding sequence of the wildtype gene but also refers to a nucleic acid sequence encoding a functional variant of the selectable marker providing the intended resistance. Hence, also truncated or mutated versions of a wild type gene are encompassed as long as they provide the intended resistance. The mammalian selectable marker gene preferably comprises foreign regulatory elements such as e.g. a strong constitutive promoter. According to a preferred embodiment, said expression cassette (Exp-MSM) comprises a gene encoding an enzymatically functional neomycin phosphotransferase (I or II) which preferably comprises foreign regulatory elements such as e.g. a strong constitutive promoter such as the SV40 promoter. This embodiment works well in combination with the use of a gene encoding an enzymatically functional DHFR as a mammalian amplifiable selectable marker gene.

Mammalian, amplifiable selectable marker genes incorporated in the expression cassette (Exp-MASM) allow selection of vector-containing host cells as well gene amplification. A non-limiting example for a mammalian amplifiable, selectable marker gene is the dihydrofolate reductase (DHFR) gene encoding the DHFR enzyme. The mammalian, amplifiable selectable marker gene preferably comprises foreign regulatory elements such as e.g. a strong constitutive promoter. Other systems currently in use are among others the glutamine synthetase (gs) system (Bebbington et al., 1992) and the histidinol driven selection system (Hartmann and Mulligan, 1988). These amplifiable markers are also selectable markers and can thus be used to select those cells that obtained the vector. DHFR and glutamine synthetase provide good results. In both cases selection occurs in the absence of the appropriate metabolite (hypoxanthine and thymidine in case of DHFR, glutamine in the case of GS), preventing growth of non-transformed cells. With amplifiable systems such as the DHFR system, expression of a recombinant protein can be increased by exposing the cells to certain agents promoting gene amplification such as e.g. methotrexate (MTX) in case of the DHFR system. E.g. the coding sequence of the wildtype DHFR gene or a DHFR mutant allowing e.g. a selection of dhfr+ cell lines may be used. A suitable inhibitor for GS promoting gene amplification is methionine sulphoximine (MSX). Exposure to MSX also results in gene amplification.

According to one embodiment, said expression cassette (Exp-MASM) comprises a gene encoding an enzymatically functional dihydrofolate reductase (DHFR) which is preferably used in conjunction with the SV40 promoter.

Accordingly, vector nucleic acids are provided wherein the expression cassettes comprise at least one promoter and/or promoter/enhancer element. Although the physical boundaries between these two control elements are not always clear, the term "promoter" usually refers to a site on the nucleic acid molecule to which an RNA polymerase and/or any associated factors binds and at which transcription is initiated. Enhancers potentiate promoter activity, temporally as well as spatially. Many promoters are transcriptionally active in a wide range of cell types. Promoters can be divided in two classes, those that function constitutively and those that are regulated by induction or derepression. Promoters used for high-level production of proteins in mammalian cells should be strong and preferably active in a wide range of cell types. Strong constitutive promoters which drive expression in many cell types include but are not limited to the adenovirus major late promoter, the human cytomegalovirus immediate early promoter, the SV40 and Rous Sarcoma virus promoter, and the murine 3-phosphoglycerate kinase promoter, EF1a. Good results are achieved with the expression vector of the present invention when the promoter and/or enhancer is either obtained from CMV and/or SV40.

According to one embodiment, the expression cassette(s) for expressing the polypeptide(s) of interest comprise(s) a stronger promoter and/or enhancer than the expression cassettes for expressing the selectable markers. This arrangement has the effect that more transcript for the polypeptide of interest is generated than for the selection markers. It is advantageous that the production of the polypeptide of interest which is secreted is dominant over the production of the selection markers, since the individual cell capacity for producing heterologous proteins is not unlimited and should thus be focused to the polypeptide of interest.

According to one embodiment, the expression cassettes (Exp-POI) and (Exp-POI') (if present) which is/are used for expressing the polypeptide of interest comprise a CMV promoter/enhancer as regulatory elements. The expression cassettes (Exp-MSM) and (Exp-MASM), which preferably express the DHFR and the neomycin marker genes, comprise an SV40 promoter or a SV40 promoter/enhancer. The CMV promoter is known to be one of the strongest promoters available for mammalian expression and leads to a very good expression rate. It is considered to give significantly more transcript than the SV40 promoter.

Most eukaryotic nascent mRNAs possess a poly A tail at their 3' end which is added during a complex process that involves cleavage of the primary transcript and a coupled polyadenylation reaction. The polyA tail is advantageous for mRNA stability and transferability. Hence, the expression cassettes of the vector according to the present invention usually comprise a polyadenylation site. There are several efficient polyA signals that can be used in mammalian expression vectors, including those derived from bovine growth hormone (bgh), mouse beta-globin, the SV40 early transcription unit and the Herpes simplex virus thymidine kinase gene. However, also synthetic polyadenylation sites are known (see e.g. the pCI-neo expression vector of Promega which is based on Levitt et al, 1989, Genes Dev. 3, (7): 1019-1025). The polyadenylation site can be selected from the group consisting of SV40polyA site, such as the SV40 late and early poly-A site (see e.g. plasmid pSV2-DHFR as described in Subramani et al, 1981, Mol. Cell. Biol. 854-864), a synthetic polyA site (see e.g. the pCI-neo expression vector of Promega which is based on Levitt et al, 1989, Genes Dev. 3, (7): 1019-1025) and a bgh polyA site (bovine growth hormone).

Furthermore, the expression cassettes may comprise an appropriate transcription termination site. This, as continued transcription from an upstream promoter through a second transcription unit may inhibit the function of the downstream promoter, a phenomenon known as promoter occlusion or transcriptional interference. This event has been described in both prokaryotes and eukaryotes. The proper placement of transcriptional termination signals between two transcription units can prevent promoter occlusion. Transcription termination sites are well characterized and their incorporation in expression vectors has been shown to have multiple beneficial effects on gene expression.

The expression cassettes may comprise an enhancer (see above) and/or an intron. According to one embodiment, the expression cassette(s) for expressing the polypeptide of interest comprise an intron. Most genes from higher eukaryotes contain introns which are removed during RNA processing. Genomic constructs are expressed more efficiently in transgenic systems than identical constructs lacking introns. Usually, introns are placed at the 5' end of the open reading frame. Accordingly, an intron may be comprised in the expression cassette(s) for expressing the polypeptide(s) of interest in order to increase the expression rate. Said intron may be located between the promoter and or promoter/enhancer element(s) and the 5' end of the open reading frame of the polypeptide to be expressed. Hence, a vector nucleic acid is provided, wherein at least the expression cassette (Exp-POI) comprises an intron which is arranged between the promoter and the start codon of the polynucleotide for expressing the polypeptide of interest. Several suitable introns are known in the state of the art that can be used in conjunction with the present invention.

According to one embodiment, the intron used in the expression cassettes for expressing the polypeptides of interest, is a synthetic intron such as the SIS or the RK intron. The RK intron is a strong synthetic intron which is preferably placed before the ATG start codon of the gene of interest. The RK intron consists of the intron donor splice site of the CMV promoter and the acceptor splice site of the mouse IgG Heavy chain variable region (see e.g. Eaton et al., 1986, Biochemistry 25, 8343-8347, Neuberger et al., 1983, EMBO J. 2(8), 1373-1378; it can be obtained from the pRK-5 vector (BD PharMingen)).

Surprisingly, the placement of an intron at the 3' end of the open reading frame of the DHFR gene has advantageous effects on the expression/amplification rate of the construct. The intron used in the DHFR expression cassette is leading to a smaller, non functional variant of the DHFR gene (Grillari et al., 2001, J. Biotechnol. 87, 59-65). Thereby the expression level of the DHFR gene is lowered. This leads to increased sensitivity for MTX and more stringent selection conditions. Accordingly, a vector nucleic acid is provided, wherein the expression cassette (MASM) comprises an intron which is located 3' of the amplifiable selectable marker gene. A suitable intron may be obtained from the pSV2-DHFR vector (see e.g. above).

Said vector may comprise at least one additional expression cassette (Exp-PSM) comprising a prokaryotic selectable marker gene. Said expression cassette (Exp-PSM) can be located between the expression cassettes (Exp-MSM) and (Exp-MASM). Said selectable marker may provide a resistance to antibiotics such as e.g. ampicillin, kanamycin, tetracycline and/or chloramphenicol. Said expression cassette (Exp-PSM) is preferably arranged in the same 5' to 3' orientation as the other expression cassettes (Exp-POI), (Exp-MSM) and (Exp-MASM).

According to one embodiment, the expression cassette (Exp-POI) and/or (Exp-POI') comprised in the vector further comprise(s)
- a polynucleotide (Pn-TAG) encoding an affinity tag located downstream of the at least one stop codon which is located downstream of the first polynucleotide and wherein said polynucleotide (Pn-TAG) is located upstream of the second polynucleotide encoding an immunoglobulin transmembrane anchor and/or
- a polynucleotide (Pn-MARKER) encoding a selectable marker.

The advantages are outlined above.

The vector nucleic acid can be transfected into the host cell in its circular form. Supercoiled vector molecules usually will be converted into linear molecules within the nucleus due to the activity of endo- and exonucleases. However, linearization of the vector nucleic acid before transfection often improves the efficiency of a stable transfection. This also as the point of linearization may be controlled if the vector is linearized prior to transfection.

Hence, according to one embodiment of the present invention the expression vector comprises a predefined restriction site, which can be used for linearization of the vector nucleic acid prior to transfection. Intelligent placement of said linearization restriction site is important, because said restriction site determines where the vector nucleic acid is opened/linearized and thus determines the order/arrangement of the expression cassettes when the construct is integrated into the genome of the eukaryotic, in particular mammalian cell.

Accordingly, the vector nucleic acid may comprise a linearization restriction site for linearizing the vector, wherein said linearization restriction site is located between the expression cassettes (Exp-MSM) and (Exp-MASM). Preferably, said linearization restriction site is unique and is only once present in the expression vector nucleic acid. E.g. a linearization restriction site can be used that is recognized by a restriction enzyme having a low cutting frequency in order to patronize that the vector is only cleaved at the linearization restriction site but not (or only rarely) e.g. within the expression cassette(s) or the vector backbone. This can e.g. be encouraged by providing a restriction site for a restriction enzyme having a recognition sequence of more than six base pairs or which recognizes sequences that are under-represented in chromosomal DNA. A suitable example is the SwaI enzyme and the vector may therefore incorporate a SwaI recognition site as unique linearization restriction site. In case said linearization restriction site is present more than once in the vector nucleic acid sequence (including the polynucleotides encoding the polypeptide of interest), or in case a restriction enzyme is used which cuts several times in the vector nucleic acid sequence, it is also within the scope of the present invention to e.g. alter/mutate the restriction sites besides the linearization restriction site which is located between the expression cassettes (Exp-MSM) and (Exp-MASM), in order to eliminate those additional restriction sites and to obtain a unique or at least rare linearization restriction site.

In case the vector is used as a standard expression vector intended e.g. as a tool for the expression of several different polypeptides, it is advantageous to provide a linearization restriction site comprising multiple recognition sites for enzymes having a low cutting frequency. The restriction enzymes chosen for linearization should preferably not cut within the expression cassettes for the selectable markers or other vector backbone sequences in order to ensure that the enzyme cuts only once for proper linearization of the vector. By providing a linearization restriction site comprising multiple recognition sites for restriction enzymes having a low cutting frequency, the user may chose a suitable restriction enzyme for linearization from the provided options in order to securely avoid restriction within the polynucleotide (Pn-POI) encoding the polypeptide of interest. However, as is outlined above, additional restriction sites may be mutated or a partial restriction digest could be performed.

Placing the linearization restriction site between the expression cassette (Exp-MSM) and the expression cassette (Exp-MASM) has the effect that the expression cassette (Exp-POI) (and further expression cassettes for expressing the polypeptides of interest—if present) is flanked 5' by the expression cassette (Exp-MASM). The expression cassette (Exp-MSM) is located 3' of the expression cassette (Exp-POI) upon linearization. Thereby, the expression cassettes (MSM) and (MASM) are separated upon linearization of the circular vector nucleic acid. If an expression cassette (Exp-PSM) for a bacterial selection marker is present (see below), the linearization restriction site is preferably placed between the expression cassettes (Exp-PSM) and (Exp-MASM). This has the effect that the bacterial selection marker gene is 3' and thus "outside" of the "mammalian" parts of the linearized vector nucleic acid. This arrangement is favorable since bacterial genes are presumably not advantageous for mammalian expression as bacterial sequences may lead to increased methylation or other silencing effects in the mammalian cells.

The polypeptide of interest is not limited to any particular protein or group of proteins, but may on the contrary be any protein, of any size, function or origin, which one desires to select and/or express by the methods described herein. Accordingly, several different polypeptides of interest may be expressed/produced. The term polypeptide refers to a molecule comprising a polymer of amino acids linked together by a peptide bond(s). Polypeptides include polypeptides of any length, including proteins (e.g. having more than 50 amino acids) and peptides (e.g. 2-49 amino acids). Polypeptides include proteins and/or peptides of any activity or bioactivity, including e.g. bioactive polypeptides such as enzymatic proteins or peptides (e.g. proteases, kinases, phosphatases), receptor proteins or peptides, transporter proteins or peptides, bactericidal and/or endotoxin-binding proteins, structural proteins or peptides, immune polypeptides, toxins, antibiotics, hormones, growth factors, vaccines or the like. Said polypeptide may be selected from the group consisting of peptide hormones, interleukins, tissue plasminogen activators, cytokines, immunoglobulins, in particular antibodies or antibody fragments or variants thereof.

As used herein, an "immunoglobulin molecule" as an example for a polypeptide of interest refers to a protein comprising one or more polypeptides substantially or partially encoded by immunoglobulin genes or fragments of immunoglobulin genes, e.g., a fragment containing one or more complementarity determining region (CDR). The recognized immunoglobulin genes include the kappa, lambda, alpha, gamma, delta, epsilon and mu constant region genes, as well as myriad immunoglobulin variable region genes. Light chains are typically classified e.g. as either kappa or lambda.

Heavy chains are typically classified e.g. as gamma, mu, alpha, delta, or epsilon, which in turn define the immunoglobulin classes, IgG, IgM, IgA, IgD and IgE, respectively. Said immunoglobulin can be of any isotype. Very often IgG (e.g. IgG1) molecules are produced/needed as therapeutic proteins. A typical immunoglobulin (antibody) structural unit comprises a tetramer. In nature, each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments which can e.g. be produced by digestion with various peptidases. An antibody fragment is any fragment of an antibody comprising at least 20 amino acids from said whole antibody, preferably at least 100 amino acids which at least still has an antigen binding capacity. The antibody fragment may comprise the binding region of the antibody such as a Fab fragment, a F(ab)2 fragment, multibodies comprising multiple binding domains such as diabodies, triabodies or tetrabodies, single domain antibodies or affibodies. An antibody variant is a derivative of an antibody or antibody fragment having the same binding function but e.g. an altered amino acid sequence. Said antibody and/or antibody fragment may comprise a murine light chain, human light chain, humanized light chain, human heavy chain and/or murine heavy chain as well as active fragments or derivatives thereof. Hence, it can be e.g. murine, humane, chimeric or humanized. While various antibody fragments are defined in terms of the digestion of an intact antibody, one of skill will appreciate that such Fab' or F(ab)2 fragments may be synthesized de novo either chemically or by utilizing recombinant DNA methodology, peptide display, or the like. Thus, the term antibody, as used herein, also includes antibody fragments either produced by the modification of whole antibodies or synthesized de novo using recombinant DNA methodologies. Antibodies also include single-armed composite monoclonal antibodies, single chain antibodies, including single chain Fv(scFv) anti-bodies in which a variable heavy and a variable light chain are joined together (directly or through a peptide linker) to form a continuous polypeptide, as well as diabodies, tribodies, and tetrabodies (see e.g. Pack et al. J Mol. Biol. 1995 Feb. 10; 246(1):28-34; Pack et al. Biotechnology (N Y). 1993 November; 11(11):1271-7; Pack & Plueckthun Biochemistry. 1992 Feb. 18; 31(6):1579-84). The antibodies are e.g., polyclonal, monoclonal, chimeric, humanized, single chain, Fab fragments, single chain Fab (Hust et al., BMC Biotechnol (2007) 7:14), fragments produced by a Fab expression library, or the like.

Polypeptides produced in accordance with the invention may be recovered by methods known in the art. For example, the polypeptide may be recovered from the nutrient medium by conventional procedures including, but not limited to, centrifugation, filtration, ultrafiltration, extraction or precipitation. Purification may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g., ammonium sulfate precipitation) or extraction. Furthermore, the polypeptide can be obtained from the host cells by cell disruption.

Also provided is a method for producing a vector nucleic acid as described above comprising the step of assembling at least one cassette (Cas-POI), preferably an expression cassette (Exp-POI), into a vector such that said cassette comprises a first polynucleotide (Pn-POI) encoding the polypeptide of interest, at least one stop codon downstream of the first polynucleotide, and a second polynucleotide downstream of the stop codon encoding an immunoglobulin transmembrane anchor or a functional variant. Said method may further comprise assembling
- an expression cassette (Exp-MSM) comprising a mammalian selectable marker gene,
- an expression cassette (Exp-MASM) comprising a mammalian amplifiable, selectable marker gene, preferably such that the expression cassette (Exp-MASM) is located 5' and the expression cassette (Exp-MSM) is located 3' of the expression cassette (Exp-POI) and wherein the expression cassettes (Exp-MASM), (Exp-POI) and (Exp-MSM) are arranged in the same 5' to 3' orientation.

Also provided is a eukaryotic, preferably a mammalian host cell which is obtained by the screening method described above. Also provided is a eukaryotic, preferably a mammalian host cell which comprises a cassette (Cas-POI) comprising a heterologous and hence foreign polynucleotide encoding a polypeptide of interest, at least one stop codon downstream of said heterologous polynucleotide and a polynucleotide downstream of the stop codon encoding an immunoglobulin transmembrane anchor or a functional variant thereof. The cassette (Cas-POI) may be introduced e.g. by the vector nucleic acid according to the present invention. Preferably, the cassette (Cas-POI) and/or the cassette (Cas-POI') is an expression cassette.

Further features of the cassette (Cas-POI) and details of suitable vectors are described above and also apply to the host cell of the present invention. Suitable eukaryotic host cells are described above. Preferably, the eukaryotic host cell is a mammalian host cell. According to one embodiment the eukaryotic host cell is not a B-cell or a B-cell derivative. Accordingly, the eukaryotic, preferably mammalian host cell is a host cell which does not naturally express the Ig alpha and Ig beta receptor chains. Furthermore, according to one embodiment, no artificial co-expression of the Ig alpha and Ig beta receptor chain occurs in said host cell. CHO cells are preferred host cells.

Also provided is a method for producing a eukaryotic host cell as described above, wherein the eukaryotic host cell is transfected with the vector nucleic acid according to the present invention and/or a heterologous nucleic acid comprising a cassette (Cas-POI) according to the present invention. There are several appropriate methods known in the prior art for introducing an expression vector into a mammalian host cell. Respective methods include but are not limited to calcium phosphate transfection, electroporation, lipofection, biolistic- and polymer-mediated genes transfer. Besides traditional random integration based methods also recombination mediated approaches can be used to transfer the cassette (Cas-POI) into the host cell genome. Such recombination methods may include use of site specific recombinases like Cre, Flp or ΦC31 (see e.g. Oumard et al, Cytotechnology (2006) 50:93-108) which can mediate directed insertion of transgenes. Alternatively, the mechanism of homologous recombination might be used to insert the cassette (Cas-POI) (reviewed in Sorrell et al, Biotechnology Advances 23 (2005) 431-469). Recombination based gene insertion allows to minimize the number of elements to be included in the heterologous nucleic acid that is transferred/introduced to the host cell. For example, an insertion locus might be used that already provides promoter and poly-A site (exogenous or endogenous) such that only the remaining elements (e.g. polynucleotide of interest, the stop codon and polynucleotide encoding an immunoglobulin transmembrane anchor of functional fragment thereof) needs to be transferred/transfected to the host cell. Even transfer of parts of the cassette (Cas-POI) would be sufficient if the missing parts would be present at the insertion site. Embodiments of a suitable expression vector according to the present invention as well as suitable host cells and polypeptides of interest are described in detail above; we refer to the above disclosure.

Also provided is a polypeptide obtained by a method according to the present invention as defined above and in the claims. Said polypeptide is preferably an immunoglobulin molecule or a fragment thereof. Polypeptides produced according to the methods of the present invention depict good stability properties. The results also show that the polypeptides are expressed in a functional form and hence in the right conformation. Accordingly, the invention also provides polypeptides obtained by the production method according to the present invention using the expression vector described in detail above. As is outlined above, polypeptides are obtained with a good yield due to the incorporated selection/screening step. The polypeptide is preferably an immunoglobulin molecule such as an antibody or a fragment thereof.

The invention is further illustrated by the following non-limiting examples, which however, describe preferred embodiments of the invention.

EXAMPLES

Example 1

Vector Construction of the Ig Transmembrane Version

A synthetic 1113 bp DNA fragment encoding part of the IgG1 constant heavy chain region plus the leaky stop codon stuffer and the Ig transmembrane and cytoplasmic domain is inserted into pBW201 (a standard vector containing an IgG1 heavy chain and kappa light chain) via Age1 and Asc1 generating pNT11 (see table 1). The nucleotide sequence of the Ig transmembrane domain used is shown in SEQ ID No: 1, the leaky stop codon stuffer is indicated. Of course, also variants of the encoded Ig transmembrane domain can be used according to the principles of the present invention which provide the same membrane anchoring function. Said variants are homologue to the encoded Ig transmembrane domain and can e.g. be obtained by conservative amino acid substitution. They share preferably at least 80%, 85%, 90% homology. Polynucleotides encoding respective variants e.g. hybridize to the shown sequence under stringent conditions.

The wt DHFR selection marker gene of pNT11 and pBW201 can be replaced by a synthetic 1252 bp fragment encoding a L23P point mutant of DHFR via SwaI and BgIII, thereby generating pNT29 and pBW478. The DHFR mutant allows the selection of dhfr+ cell lines.

The FACS vectors (pNT11, pNT29) are based on the standard vectors for antibody expression (pBW201, pBW478). pNT11 and pBW201 are differing from pNT29 and pBW478 in the DHFR selection marker cassette they are carrying. Apart from that the backbones are identical. The vector has a mono-cistronic "tandem" setup and contains antibody light and heavy chain expression cassettes, both driven by the CMV promoter/enhancer. The only modification to generate the FACS vectors was the insertion of an IgG1 transmembrane and cytoplasmic domain 3' of the antibody heavy chain (HC) cDNA. A short stuffer with a leaky translation termination signal is placed between HC and transmembrane domain. The sequence environment selected for the stop codon is expected to lead to a read-through of up to 5%. All four vectors are coding for the same human IgG antibody.

As is outlined above, the vector nucleic acids used for expression and in particular the orientation and arrangement of the vector elements chosen allow the very efficient expression of immunoglobulin molecules. Suitable vectors that can be used in conjunction with the present invention and which are described above are illustrated in the following table (the arrows indicate the 5' to 3' orientation of the genetic elements):

TABLE 1

Vector map pNT11 - "FACS vector"
CMVprom/enhan →
RK-intron →
mAB-LC →
SV40polyA →
CMV prom/enhan →
RK-intron →
mAB-HC →
Stuffer + leaky stop codon
Ig transmembrane domain and cyto-plasmatic domain →
SV40polyA →
Phage f1 region →
SV40prom/enhan →
Neo →
Synth polyA
Amp →
SV40prom/enhan →
DHFR →
SV40pA →

The abbreviations in table 1 have the regular meaning as apparent for the person of skill in the art and as described above, and have in particular the following meanings:
CMVprom/enh=human cytomegalovirus immediate early promoter/enhancer
RK-intron=comprises the intron donor splice site of the CMV promoter and the acceptor splice site of the mouse IgG Heavy chain variable region (see e.g. Eaton et al., 1986, Biochemistry 25, 8343-8347, Neuberger et al., 1983, EMBO J. 2(8), 1373-1378; it can be obtained from the pRK-5 vector (BD PharMingen))
mAB-LC=monoclonal antibody light chain
mAB-HC=monoclonal antibody heavy chain
SV40polyA=SV40 polyA site
SV40prom/enhan=SV40 promotor/enhancer
Neo=neomycin phosphotransferase
Synth polyA=synthetic polyadenylation site
Amp=beta lactamase antibiotic resistance gene
DHFR=dihydrofolate reductase gene.

Example 2

Transfection and Selection of CHO-Cells

Cell cultivation, transfection and screening is carried out in shake flasks using suspension growing CHO cells in a proprietary, chemically defined culture medium. Cells are either transfected by lipofection or electroporation (nucleofection) following the manufacturer's instructions. Transfection efficiency is checked by transfecting a GFP (green fluorescence protein)-reporter plasmid and flow cytometric analysis of the transfected cells. Depending on the cell viability, selection is started 24-48 h after transfection by adding G418 containing selective medium to the cells. As soon as cells recover to a viability of above 80%, a second selection step is applied by passaging the cells to G418 free, MTX (methotrexate) containing medium. After recovery of the cells from the MTX selection, cultivation is continued in MTX containing medium throughout FACS enrichment cycles, FACS cloning or limited dilution cloning and screening.

Cell viability and growth are monitored using an automated system (ViCell, Beckmann Coulter).

Example 3

FACS Analysis, Enrichment and Cloning of Cells

Labeling of cells: 2×10E7 cells per transfected pool are centrifuged and washed with 5 mL of chilled PBS (phosphate buffered saline) and resuspended in 1 mL of cold PBS. A suitable amount of FITC (fluorescein isothiocyanate) labeled anti-IgG antibody is added to the cells and is incubated on ice for 30 minutes in the dark. Subsequently, cells are washed twice at room temperature with 5 mL PBS, resuspended in 1 mL PBS, filtrated and dispensed into a FACS tube for analysis, sorting and cloning.

Analysis, sorting and cloning of cells: The cell sorting is performed with a FACSAria (Becton Dickinson) equipped with an Automatic Cell Deposition Unit (ACDU) using FACSDiva software. A low powered air-cooled and solid-state laser (Coherent® Sapphire™ solide state) tuned to 488 nm is used to excite fluorescein dyes bound to the secondary antibody. The relative FITC fluorescence intensity is measured on E detector through a 530/30 BP filter. Five percents of the highest FITC fluorescent cells are gated and sorted either in block or as single cells in 96 well plates.

Example 4

Determination of Clonal Productivity and Stability

Productivity of clones is analyzed in batch and fed batch experiments using different formats. Initial clone screening is performed in 24-well plate batch assays by seeding cells to shaken 24-well plates. Antibody concentrations in the cell culture supernatant are determined by protein-A HPLC 10d after starting the culture. The highest producing clones are also analyzed in shake flask models in batch and fed batch mode. Batch cultures are seeded in shake flask 500 with 100 mL working volume and are cultivated in a shaker cabinet (not humidified) at 150 rpm and 10% CO2. Viability of cells should be >90% when starting the assay. The seeding cell density is $2\times10^5$ c/mL. Product concentration/cell number/viability determination took place at day 3-7, 10 and 13. Fed batch experiments are done using the same conditions but with a starting cell density of $4\times10^5$ c/mL and with regular adding of feeds. Clonal stability is evaluated by culturing the cells over a period of 14 weeks with productivity measurements using the shake flask batch model every two weeks.

Example 5

Analysis of Transiently Transfected Cells

To test whether membrane bound translation products are present on the cell surface after transfection with the new FACS vector (here pNT11 or pNT29), transiently transfected cells are analyzed by immunostaining and flow cytometry. 48 h after transfection, cells are stained with a FITC-labeled antibody directed against human IgG. Cells transfected with a GFP expression vector are used as a transfection control, the transfection efficiency is calculated to be about 60%. Un-transfected cells and cells transfected with the standard vector (not comprising a transmembrane domain) do not show significant levels of surface associated antibody, while 16% of the cells transfected with the FACS vector are stained above background level. This shows that the fusion peptide, here an antibody molecule, anchored to the cell membrane can be detected on the cell surface.

Example 6

Analysis and Enrichment of Stable Transfected Cells

Having shown presence of membrane bound antibody on transiently transfected cells the surface expression level and distribution in selected pools of transfected cells is analysed. Thereby, it can be shown that producing cells can be selectively enriched by FACS sorting. Therefore, cells after transfection are selected with G418 and subsequently with MTX. The resulting pools of resistant cells are stained with FITC labelled anti-IgG antibody and analyzed by flow-cytometry. As a control, un-transfected cells are stained and analyzed. Subpopulations of positive cells are detected in the selected pools transfected with the FACS vector. The distribution of positive cells thereby differed between the two analyzed pools. To assess whether high producing cells can be enriched based on their fluorescence signal (and hence allow a quantitative selection), cells having the highest fluorescence intensity are sorted (top 5%) from each of the two pools and sub-cultured to compare the productivity with the pool before enrichment.

Example 7

Analysis of Productivity of Enriched and Non Enriched Cells

Productivity analyses of the selected pools before and after flow-cytometry enrichment are done in shake flask batch cultures to compare the end-product concentration at day 13. At day 13 the supernatant is harvested and analyzed for IgG content by Protein-A-HPLC. Both pools show a significant increase of production level already after performing one FACS enrichment cycle according to the teachings of the present invention. While product concentration for pool 1 increases by a factor of approximately 2, pool 2 increases by a factor of almost 10 showing that high producing cells are selectively detected during staining and sorting.

Already in the first enrichment cycle antibody concentrations of almost 250 mg/l can be obtained.

Example 8

Flow-Cytrometry Based Selective Cloning of High Producing Cells

Flow-cytrometry can be used to sort and seed individual stained cells according to their staining profile. To analyze whether such selective cloning results in higher number of high producing clones than cloning by limiting dilution, clones are generated using both methods and productivity is analyzed in 24-well plate batch cultures. Batch cultures in 24-well plates are done and at day 10 supernatants are harvested and measured for IgG content by Protein-A-HPLC. The results are as follows:

TABLE 2

| | FACS sorting versus limited dilution (LD) | | | | | |
|---|---|---|---|---|---|---|
| Method | 0-25 mg/l | 26-50 mg/l | 51-75 mg/l | 76-100 mg/l | 101-125 mg/l | 126-150 mg/l |
| LD - obtained clones | 12 | 0 | 1 | 0 | 1 | 0 |
| FACS - obtained clones | 2 | 2 | 2 | 2 | 0 | 1 |

The flow-cytrometry derived clones have a higher average productivity compared to the liming dilution derived clones, which is also reflected in the clonal distribution of the productivity range.

Example 9

Comparison of FACS and Standard Vector

To confirm the beneficial effect of flow-cytometry enrichment of transfected cells and to compare use of the FACS vector (pNT29) with a standard vector, cells are transfected and selected with G418 and MTX. Three cell pools transfected with the FACS vector (samples 1, 2 and 3) and three cell pools transfected with the standard vector (samples 7, 9 and 9) are analyzed by flow cytometry and the 5% having the highest staining signal are sorted. Shake flask batch cultures are done to compare the increase of product concentration after enrichment. Transfected and selected pools are stained and sorted by flow-cytrometry to enrich the top 5% based on the fluorescence intensity. Before and after enrichment, shake flask batch cultures are done and after 13 days supernatants are analyzed by Protein-A-HPLC. The results are as follows (approximately):

TABLE 3

| Results obtained with the FACS vector | |
|---|---|
| Sample | Product concentration |
| Sample 1; FACS vector, before enrichment | 10 mg/l |
| Sample 1; FACS vector, 1st enrichment | 55 mg/ml |
| Sample 1; FACS 2nd enrichment | 100 mg/ml |
| Sample 1; FACS vector, 3rd enrichment | 365 mg/ml |

TABLE 3-continued

Results obtained with the FACS vector

| Sample | Product concentration |
|---|---|
| Sample 2; FACS vector, before enrichment | 40 mg/ml |
| Sample 2; FACS vector, 1st enrichment | 65 mg/ml |
| Sample 2; FACS vector, 2nd enrichment | 90 mg/ml |
| Sample 2; FACS vector, 3rd enrichment | 340 mg/ml |
| Sample 3; FACS vector, before enrichment | 15 mg/ml |
| Sample 3; FACS vector, 1st enrichment | 95 mg/ml |
| Sample 3; FACS vector, 2nd enrichment | 155 mg/ml |
| Sample 3; FACS vector, 3rd enrichment | 85 mg/ml |

TABLE 4

Results obtained with the Standard vector

| Sample | Product concentration |
|---|---|
| Sample 7; Standard vector, before enrichment | 40 mg/l |
| Sample 7; Standard vector, 1st enrichment | 55 mg/ml |
| Sample 7; Standard 2nd enrichment | 50 mg/ml |
| Sample 7; Standard vector, 3rd enrichment | 25 mg/ml |
| Sample 8; Standard vector, before enrichment | 5 mg/ml |
| Sample 8; Standard vector, 1st enrichment | 10 mg/ml |
| Sample 8; Standard vector, 2nd enrichment | 12 mg/ml |
| Sample 8; Standard vector, 3rd enrichment | 15 mg/ml |
| Sample 9; Standard vector, before enrichment | 5 mg/ml |
| Sample 9; Standard vector, 1st enrichment | 2 mg/ml |
| Sample 9; Standard vector, 2nd enrichment | 10 mg/ml |
| Sample 9; Standard vector, 3rd enrichment | 10 mg/ml |

As is demonstrated by the results, the production level of FACS vector transfected cells increases significantly for the tested three pools, while in case of the standard vector only one pool showed a significant increase in product concentration. The average of product concentrations after enrichment with the FACS vector is significantly higher as with the standard vector. Two further sequential FACS enrichment cycles are done to enrich high producing cells showing that only in case of the FACS vector productivity of the cell populations is increased. Finally, product concentrations can be increased by 4- to 30-fold.

For comparison of the suitability of both vectors for selective cloning, clones from non-enriched pools with comparable productivity are selectively sorted by flow-cytometry. Subsequently, productivity of the clones is analyzed in 24-well batch cultures. Clones derived from FACS vector transfected pools are found to have a higher average expression level as clones from standard vector transfected pools. The clonal distribution of productivity shows that in case of the FACS vector a higher number of good producing clones is obtained (see table 5):

TABLE 5

Standard vector versus FACS vector (pNT29)

| Method | 0-50 mg/l | 51-100 mg/l | 101-150 mg/l | 151-200 mg/l | 201-250 mg/l | 251-300 mg/l | 301-350 mg/ml |
|---|---|---|---|---|---|---|---|
| Standard vector | 31 | 7 | 0 | 2 | 0 | 1 | 0 |
| FACS vector | 21 | 20 | 4 | 4 | 4 | 2 | 1 |

Example 10

Further Comparisons Between the FACS Vector and Standard Expression Vectors a) Vector Construction The vectors pBW201, pNT11, pBW478 and pNT29 are obtained as described in example 1.

b) Transfection, Selection and Cloning of CHO Cells

This is done as described in example 2.

c) FACS Analysis, Enrichment and Cloning of Cells

This is done as described in example 3.

d) Determination of Antibody Production and Clonal Stability

The productivity of clones and pools is analyzed in batch and fed batch experiments using different formats. Pools before and after FACS enrichment are analyzed in shake flask batch assays by seeding $1\times10^5$ cells per mL (c/mL) in 50 mL working volume using shake flasks with 250 mL capacity. IgG content is analyzed by Protein-A HPLC from samples taken at day 13 of the batch culture. Initial screening of clones is performed in 24-well plate batch assays by seeding cells into shaken 24-well plates. Antibody concentrations in the cell culture supernatant are determined by quantitative Protein A-HPLC 10 days after starting the culture. The highest producing clones are analyzed in shake flask models in batch and fed batch mode. Batch cultures are seeded into shake flasks (500 mL capacity) with 100 mL working volume and are cultivated in a shaker cabinet (not humidified) at 150 rpm, 36.5° C. and 10% $CO_2$. Viability of cells is >90% when starting the assay. The seeding cell density is $2\times10^5$ c/mL. Antibody concentrations, cell number and viability are determined on days 3-7, 10 and 13. Fed batch experiments are done using the same conditions but with a runtime of 17 days and with a starting cell density of $4\times10^5$ c/mL and with regular addition of feeds starting at viable cell densities above $7\times10^6$ c/mL. Clonal stability is evaluated by culturing the cells over a period of 12 weeks with productivity measurements using the shake flask batch model every two weeks.

e) Analysis and Enrichment of Stable Transfected Cells

The surface expression in stably transfected cell populations is analysed to test whether producing cells can be selectively enriched by FACS-sorting. Therefore, cells after transfection are selected with G418 and subsequently with MTX. The resulting pools (10 per vector) of resistant cells are stained as described above and analyzed by flow-cytometry. With the used staining protocol positive subpopulations of cells could be detected in both, pBW478 and pNT29 transfected cell pools. As expected, a higher proportion of FACS positive cells is found with the FACS vector.

To show that high producing cells can be enriched based on their fluorescence signal, cells having the highest fluorescence intensity are sorted (top 5%) from the individual cell pools and sub-cultured to compare the productivity with the pool before enrichment. A second cycle of enrichment is performed after expansion and pooling of the one times sorted cell populations. The percentage of staining positive cells surprisingly increased most with the standard vector in the first enrichment cycle. FACS-vector transfected pools showed similar enrichment factors with the used staining protocol and generally, significant pool to pool variation was observed. After the second enrichment cycle, almost homogeneously FACS positive cell populations are obtained (see Table 6a and 6b).

Table 6a and 6B: Average Staining Results and Productivities Before and after Sorting again, there is substantial variation between individual pools (see Table 6b). Surprisingly, the productivity of the standard vector transfected pools is not higher compared to the FACS vector transfected ones although a much higher level of FACS staining positive cells was seen before. By sorting a second time from the pooled sorted cell populations, no further improvement of productivity is achieved with the standard vector. In contrast, a lower productivity is obtained although the FACS-staining result suggested that almost 100% of the cells should be producing antibody (see Table 6a). Productivity of FACS-vector transfected pools could be significantly improved by sorting a second time. The used FACS procedure leads to more selective enrichment of high producing cells with a productivity increase of about at least 8-fold compared to unsorted population and at least 2-fold compared to the pools after one sorting.

g) Flow-Cytometry Based Selective Cloning of High Producing Cells

Flow-cytometry can be used to sort and seed individual stained cells according to their staining profile. To analyze whether such selective cloning results in higher number of high producing clones when using the FACS-vector compared to the standard vector, clones are generated using both methods and productivity is analyzed in 24-well plate batch cultures.

In a first round, cells are directly FACS-cloned from the MTX selected cell pools without any pre-enrichment step. Three pools per vector are chosen based on their staining profile. Clones are generated from the top 5% of the stained cell pools and in total about 500 clones are analyzed. While

TABLE 6a

FACS analysis of stained cells before and after FACS enrichment cycles

| % cells above background | pBW478 (reference vector) | | | pNT29 (FACS vector) | | |
|---|---|---|---|---|---|---|
| FITC staining | No FACS | 1x FACS | 2x FACS | No FACS | 1x FACS | 2x FACS |
| AVG | 5.9 | 83.2 | 90.4 | 14.2 | 46.6 | 90.5 |
| STDD | 3.396403 | 15.80158 | 1.126795 | 8.974284 | 13.51148 | 1.422439 |

Table 6a: Transfected and selected cell pools were stained for surface IgG. Average percentage of cells stained above the level of untransfected cells is shown. Before enrichment a higher percentage of positive cells is found with the FACS vector. After the first enrichment cycle of the top 5%, the proportion of staining positive cells was highest with the standard vector. After the second enrichment cycle, greater that 90% of all cells were positive with both approaches. Abbreviations: AVG: Average and STDD: Standard deviation.

TABLE 6b

Productivities of in shake flask batch model before and after FACS enrichment cycles

| mAb | pBW478 (reference vector) | | | pNT29 (FACS vector) | | |
|---|---|---|---|---|---|---|
| (mg/L) | No FACS | 1x FACS | 2x FACS | No FACS | 1x FACS | 2x FACS |
| AVG | 38.5 | 123.4 | 68.3 | 46.5 | 171.8 | 363 |
| STDD | 17.66509 | 101.8563 | 6.592926 | 15.30614 | 114.1936 | 70.19259 |

Table 6b: Productivity of cell pools is analyzed from shake flask batch cultures by Protein-A HPLC at day 13 of the culture. The first enrichment cycle led to a significant increase of productivity in both cases. After the second enrichment, only FACS vector transfected cell pools showed additional increase in productivity.

f) Analysis of Productivity of Enriched and Non Enriched Cells

Productivity analysis of the selected pools before and after flow-cytometry enrichment are done in shake flask batch cultures to compare the end-titers at day 13. Productivity of the pools before enrichment is in a very comparable range for both vectors used. With the first enrichment cycle on the individual pools significant improvement of the average productivity is achieved with all approaches and average productivity of clones with the reference vector was 39 mg/L, FACS-vector clones produced an average of 87 mg/L. As shown in Table 7a, this is also reflected by the clonal distribution which confirms that a much higher proportion of high producing clones is obtained with the FACS-vector. Interestingly, one out of the over 270 clones analyzed from the standard vector transfection had an almost 2-fold higher productivity compared to the others. This exceptional clone is designated LP. Identifying such a high producing cell clone with the standard vector setup in combination with a FACS screening procedure is thus generally possible. However, it is a very rare and thus lucky event. This is also the decisive difference to the selection process according to the teachings of the present invention. While the standard set up allows the selection of (very) high producers only in exceptional and thus rare cases, the method according to the present invention allows the selection of (very) high producers reproducibly and thus reliably.

A second FACS-cloning experiment is performed starting from the 10 pooled populations per vector after the first enrichment cycle. This time approximately 240 clones are screened in 24-well batch cultures. Again, clones obtained with the FACS-vector have a much higher average productivity than the reference standard vector. No improvement compared to cloning without pre-enrichment is achieved with the reference vector at an average clone productivity of 40 mg/L. The LP clone was not identified again. In case of the FACS vector transfected clones, an average productivity of 275 mg/L was obtained with the used FACS method. The clonal distribution clearly demonstrates the superiority of the FACS-vector setup with regards to selective cloning of high producers (see Table 7b).

Table 7a and 7b: Comparison of Productivity of Clones

TABLE 7a 24-well-Batch - Clonal distribution

|  | pBW478 | pNT29 |
|---|---|---|
| 0-50 mg/L | 196 | 163 |
| 51-100 mg/L | 70 | 22 |
| 101-150 mg/L | 8 | 11 |
| 151-200 mg/L | 2 | 5 |
| 201-250 mg/L | 0 | 13 |
| 251-300 mg/L | 2 | 9 |
| 301-350 mg/L | 1 | 10 |
| 351-400 mg/L | 0 | 6 |
| 401-450 mg/L | 0 | 5 |
| 451-500 mg/L | 0 | 2 |
| 501-550 mg/L | 0 | 1 |
| 551-600 mg/L | 1 | 0 |

Table 7a:
Clones are generated by flow-cytrometry from the top 5% of the three stained cell pools with the highest percentage of staining positive cells after selection. For productivity assessment, batch cultures in 24-well plates were done and at day 10 supernatants were harvested and measured for IgG content by Protein-A-HPLC. Shown here is the clonal distribution of the productivity range. A significantly higher proportion of high producing clones is obtained when using the FACS vector (pNT29).

TABLE 7b 24-well-Batch: FACS Cloning Pooled pools

|  | pBW478 | pNT29 |
|---|---|---|
| 0-50 mg/L | 102 | 22 |
| 51-100 mg/L | 17 | 2 |
| 101-150 mg/L | 13 | 5 |
| 151-200 mg/L | 5 | 3 |
| 201-250 mg/L | 2 | 7 |
| 251-300 mg/L | 0 | 11 |
| 301-350 mg/L | 0 | 11 |
| 351-400 mg/L | 0 | 15 |
| 401-450 mg/L | 0 | 9 |
| 451-500 mg/L | 0 | 7 |
| 501-550 mg/L | 0 | 7 |
| 551-600 mg/L | 0 | 1 |
| 601-650 mg/L | 0 | 3 |

Table 7b:
Clones obtained by FACS cloning from the top 5% of stained combined pools after one enrichment cycle were analyzed. No benefit the from pre-enrichment was found for reference vector (pBW478) transfected cells, while in case of FACS vector (pNT29) transfected cells, pre-enrichment led to a significant reduction of non-producers and to an increase of the average productivity of clones.

h) Characterisation of Clones

The LP clone derived from the standard vector as well as 10 high producing FACS-vector clones are expanded to shake flasks and tested in generic shake flask batch and fed-batch models to evaluate their manufacturing potential.

Productivity in batch cultures is found to be about the same in the range of 1 g/L for all clones tested. Fed-batch productivities are also very comparable for all clones and in the range of 3.5-4 g/L (see Table 8). No significant difference in growth parameters are observed when comparing the FACS-vector transfected clones with reference vector transfected clones (LP and clones from previous experiments). Also, production stability is found to be high for the FACS-vector derived clones, only one out of 10 analyzed clones showed a drop of productivity greater than 25% after 12 weeks in culture which is a lower ratio of unstable clones as it was observed with the reference standard vector in previous experiments (data not shown).

TABLE 8

Pool productivities: Fed batch shake flask (SF) model

| | mAb (g/L) | |
|---|---|---|
|  | SF batch | SF fed batch |
| 1 = LP | 1.1 | 4.3 |
| 2 | 0.9 | 3.7 |
| 3 | 1.0 | 3.9 |
| 4 | 1.0 | 3.8 |
| 5 | 1.0 | 3.8 |
| 6 | 1.0 | 3.9 |
| 7 | 1.2 | 3.3 |
| 8 | 1.0 | 3.8 |
| 9 | 0.9 | 3.6 |
| 10 | 1.0 | 3.7 |
| 11 | 0.9 | 3.3 |

Table 8:
The highest producing clone obtained with the standard vector (pBW478) and 10 clones derived from the FACS vector (pNT29) are analyzed in batch and fed batch shake flask cultures. IgG content is analyzed by Protein-A HPLC at day 13 (batch cultures) or day 17 (fed batch cultures). All analyzed cones produce in a comparable range.

Example 11

Large Scale Production of Polypeptides with Transfected CHO Cells

The production of polypeptides in large scale can be done for example in wave, glass or stainless steel bioreactors. For that purpose the cells are expanded, usually starting from a single frozen vial, for example a vial from a Master Cell Bank. The cells are thawed and expanded through several steps. Bioreactors of different scale are inoculated with appropriate amounts of cells. The cell density can be increased by adding feed solutions and additives to the bioreactor. Cells are kept at a high viability for a prolonged time. Product concentrations in the reactor ranging from a few hundred milligrams per litre up to several grams per litre are achieved in the large scale. Purification can be done by standard chromatography methodology, which can include affinity, ion exchange, hydrophobic interaction or size exclusion chromatography steps. The size of the bioreactor can be up to several thousand litres volume in the final scale (see also e.g. F. Wurm, Nature Biotechnology Vol. 22, 11, 2004, 1393-1398).

The invention claimed is:

1. A method for producing a polypeptide of interest with high yield, the method comprising:
   a) providing a plurality of mammalian host cells comprising a heterologous nucleic acid comprising at least one cassette (Cas-POI) comprising a first polynucleotide (Pn-POI) encoding the polypeptide of interest, at least one leaky stop codon downstream of the first polynucleotide, and a second polynucleotide downstream of the leaky stop codon encoding an immunoglobulin transmembrane anchor comprising a cytoplasmic domain;
   b) cultivating the mammalian host cells to allow expression of the polypeptide of interest such that at least a portion of the polypeptide of interest is expressed as a fusion polypeptide comprising the immunoglobulin transmembrane anchor directly anchored to the cell membrane comprising a cytoplasmic domain, wherein at least a portion of said fusion polypeptide comprising the immunoglobulin transmembrane anchor is displayed on the surface of said mammalian host cells to allow binding of a detection compound;
   c) selecting at least one of the plurality of mammalian host cells based upon to the presence or amount of the fusion polypeptide displayed on the cell surface;
   d) culturing the selected mammalian host cell in culture medium under conditions that allow for expression of the polypeptide of interest wherein the polypeptide of interest is secreted into the culture medium; and
   e) obtaining the polypeptide of interest from the culture medium.

2. The method according to claim 1, wherein the immunoglobulin transmembrane anchor is selected from the group consisting of
   a) a transmembrane anchor derived from IgA, IgE, IgM, IgG and/or IgD, and
   b) an immunoglobulin transmembrane anchor comprising a sequence as shown in SEQ ID NO: 2, SEQ ID NO: 3, SEQ ID NO: 4, SEQ ID NO: 5, SEQ ID NO: 6 and/or SEQ ID NO: 7.

3. The method according to claim 1, wherein step c) comprises contacting the plurality of mammalian host cells with a detection compound binding the fusion polypeptide and selecting at least one mammalian host cell based upon the presence or amount of the bound detection compound.

4. The method according to claim 1, wherein two or more selection cycles are performed, wherein in each selection cycle at least one mammalian host cell is selected based upon the presence or amount of the fusion polypeptide displayed on the cell surface.

5. The method according to claim 3, wherein binding of the detection compound to the surface of the mammalian host cell is detected by flow cytometry.

6. A method for producing a polypeptide of interest, comprising culturing a mammalian host cell which comprises at least one cassette comprising:
   a) at least a first polynucleotide encoding a polypeptide of interest;
   b) at least one leaky stop codon downstream of the first polynucleotide; and
   c) a second polynucleotide downstream of the leaky stop codon encoding an immunoglobulin transmembrane anchor comprising a cytoplasmic domain,
   wherein at least a portion of said immunoglobulin transmembrane anchor is displayed on the surface of said mammalian host cells to allow binding of an immunoglobulin.

7. The method for producing a polypeptide of interest according to claim 1, further comprising one or both of the following steps:
   a) purifying the expressed polypeptide; and
   b) further processing or modifying the expressed polypeptide.

8. The method for producing a polypeptide of interest according to claim 6, further comprising at least one step selected from the steps:
   obtaining the polypeptide from the cell culture;
   obtaining the polypeptide from the culture medium wherein the polypeptide is secreted into the culture medium;
   isolating the expressed polypeptide;
   purifying the expressed polypeptide; and
   further processing or modifying the expressed polypeptide.

* * * * *

UNITED STATES PATENT AND TRADEMARK OFFICE
CERTIFICATE OF CORRECTION

Page 1 of 2

PATENT NO. : 9,758,779 B2
APPLICATION NO. : 13/060974
DATED : September 12, 2017
INVENTOR(S) : Thomas Jostock et al.

It is certified that error appears in the above-identified patent and that said Letters Patent is hereby corrected as shown below:

On the Title Page

Under ABSTRACT "8 Claims, No Drawings" should read --6 Claims, No Drawings--.

In the Claims

Column 39, Line 15 - Column 40, Line 55 approx., should read:

--1. A method for producing a polypeptide of interest with high yield, the method comprising:
a) providing a plurality of mammalian host cells comprising a heterologous nucleic acid comprising at least one cassette (Cas-POI) comprising a first polynucleotide (Pn-POI) encoding the polypeptide of interest, at least one leaky stop codon downstream of the first polynucleotide, and a second polynucleotide downstream of the leaky stop codon encoding an immunoglobulin transmembrane anchor comprising a cytoplasmic domain;
b) cultivating the mammalian host cells to allow expression of the polypeptide of interest such that at least a portion of the polypeptide of interest is expressed as a fusion polypeptide comprising the immunoglobulin transmembrane anchor directly anchored to the cell membrane comprising a cytoplasmic domain, wherein at least a portion of said fusion polypeptide comprising the immunoglobulin transmembrane anchor is displayed on the surface of said mammalian host cells to allow binding of detection compound;
c) selecting at least one of the plurality of mammalian host cells based upon to the presence or amount of the fusion polypeptide displayed on the cell surface;
d) culturing the selected mammalian host cell in culture medium under conditions that allow for expression of the polypeptide of interest wherein the polypeptide of interest is secreted into the culture medium; and
e) obtaining the polypeptide of interest from the culture medium.

2. The method according to claim 1, wherein the immunoglobulin transmembrane anchor is selected from the group consisting of
a) a transmembrane anchor derived from IgA, IgE, IgM, IgG and/or IgD, and Signed and Sealed this
Nineteenth Day of November, 2019

Andrei Iancu
*Director of the United States Patent and Trademark Office* b) an immunoglobulin transmembrane anchor comprising a sequence as shown in SEQ ID NO: 2, SEQ ID NO: 3, SEQ ID NO: 4, SEQ ID NO: 5, SEQ ID NO: 6 and/or SEQ ID NO: 7.

3. The method according to claim 1, wherein step c) comprises contacting the plurality of mammalian host cells with a detection compound binding the fusion polypeptide and selecting at least one mammalian host cell based upon the presence or amount of the bound detection compound.

4. The method according to claim 1, wherein two or more selection cycles are performed, wherein in each selection cycle at least one mammalian host cell is selected based upon the presence or amount of the fusion polypeptide displayed on the cell surface.

5. The method according to claim 3, wherein binding of the detection compound to the surface of the mammalian host cell is detected by flow cytometry.

6. The method for producing a polypeptide of interest according to claim 1, further comprising one or both of the following steps:
a) purifying the expressed polypeptide; and
b) further processing or modifying the expressed polypeptide.--.

SEQUENCE LISTING

<160> NUMBER OF SEQ ID NOS: 7

<210> SEQ ID NO 1
<211> LENGTH: 219
<212> TYPE: DNA
<213> ORGANISM: Artificial Sequence
<220> FEATURE:
<223> OTHER INFORMATION: polynucleotide sequence of a human IgG1
      transmembrane domain including stuffer
<220> FEATURE:
<221> NAME/KEY: Misc_feature
<222> LOCATION: (1)..(7)
<223> OTHER INFORMATION: Stuffer including stop codon
<220> FEATURE:
<221> NAME/KEY: Misc_feature
<222> LOCATION: (1)..(3)
<223> OTHER INFORMATION: Stop codon
<220> FEATURE:
<221> NAME/KEY: Misc_feature
<222> LOCATION: (4)..(6)
<223> OTHER INFORMATION: Additional codon to mediate leakyness of the
      upstream stop codon

<400> SEQUENCE: 1
tgactagagc tgcaactgga ggagagctgt gcggaggcgc aggacgggga gctggacggg      60
ctgtggacga ccatcaccat cttcatcaca ctcttcctgt taagcgtgtg ctacagtgcc     120
accgtcacct tcttcaaggt gaagtggatc ttctcctcgg tggtggacct gaagcagacc     180
atcatccccg actacaggaa catgatcgga caggggggcc                           219

<210> SEQ ID NO 2
<211> LENGTH: 25
<212> TYPE: PRT
<213> ORGANISM: Artificial Sequence
<220> FEATURE:
<223> OTHER INFORMATION: polypeptide sequence of a putative
      transmembrane region derived from a human IgG1 transmembrane
      domain

<400> SEQUENCE: 2

Leu Trp Thr Thr Ile Thr Ile Phe Ile Thr Leu Phe Leu Leu Ser Val
1               5                   10                  15

Cys Tyr Ser Ala Thr Val Thr Phe Phe
            20                  25

<210> SEQ ID NO 3
<211> LENGTH: 73
<212> TYPE: PRT
<213> ORGANISM: Artificial Sequence
<220> FEATURE:
<223> OTHER INFORMATION: Polypeptide sequence of an Ig transmembrane
      region derived from the human IgG1 transmembrane domain comprising
      the amino acids derived from the stop codon and the adjacent
      codon, a connecting region and a putative transmembrane region
<220> FEATURE:
<221> NAME/KEY: Misc_feature
<222> LOCATION: (1)..(2)
<223> OTHER INFORMATION: amino acids that are most likely used at the
      TGA stop codon and the downstream codon in case of read through
<220> FEATURE:
<221> NAME/KEY: Misc_feature
<222> LOCATION: (3)..(20)
<223> OTHER INFORMATION: Putative connecting region derived from the
      human IgG1 transmembrane domain
<220> FEATURE:
<221> NAME/KEY: Misc_feature
<222> LOCATION: (21)..(45)
<223> OTHER INFORMATION: Putative transmembrane region derived from the
      human IgG1 transmembrane domain - said region may also be deemed
      as comprising the next two amino acids
<220> FEATURE:

<221> NAME/KEY: Misc_feature
<222> LOCATION: (46)..(73)
<223> OTHER INFORMATION: Putative cytoplasmatic region derived from
      human IgG1 - the first two amino acids may also be deemed as
      belonging to the transmembrane domain

<400> SEQUENCE: 3

Trp Leu Glu Leu Gln Leu Glu Glu Ser Cys Ala Glu Ala Gln Asp Gly
1               5                   10                  15

Glu Leu Asp Gly Leu Trp Thr Thr Ile Thr Ile Phe Ile Thr Leu Phe
            20                  25                  30

Leu Leu Ser Val Cys Tyr Ser Ala Thr Val Thr Phe Phe Lys Val Lys
        35                  40                  45

Trp Ile Phe Ser Ser Val Val Asp Leu Lys Gln Thr Ile Ile Pro Asp
    50                  55                  60

Tyr Arg Asn Met Ile Gly Gln Gly Ala
65                  70

<210> SEQ ID NO 4
<211> LENGTH: 28
<212> TYPE: PRT
<213> ORGANISM: Artificial Sequence
<220> FEATURE:
<223> OTHER INFORMATION: Cytoplasmatic region derived from an human
      IgG1 transmembrane domain

<400> SEQUENCE: 4

Lys Val Lys Trp Ile Phe Ser Ser Val Val Asp Leu Lys Gln Thr Ile
1               5                   10                  15

Ile Pro Asp Tyr Arg Asn Met Ile Gly Gln Gly Ala
            20                  25

<210> SEQ ID NO 5
<211> LENGTH: 18
<212> TYPE: PRT
<213> ORGANISM: Artificial Sequence
<220> FEATURE:
<223> OTHER INFORMATION: Connecting region derived from the human IgG1
      transmembrane domain

<400> SEQUENCE: 5

Glu Leu Gln Leu Glu Glu Ser Cys Ala Glu Ala Gln Asp Gly Glu Leu
1               5                   10                  15

Asp Gly

<210> SEQ ID NO 6
<211> LENGTH: 26
<212> TYPE: PRT
<213> ORGANISM: Artificial Sequence
<220> FEATURE:
<223> OTHER INFORMATION: Cytoplasmatic region derived from an human IgG1
      transmembrane domain

<400> SEQUENCE: 6

Lys Trp Ile Phe Ser Ser Val Val Asp Leu Lys Gln Thr Ile Ile Pro
1               5                   10                  15

Asp Tyr Arg Asn Met Ile Gly Gln Gly Ala
            20                  25

<210> SEQ ID NO 7
<211> LENGTH: 27
<212> TYPE: PRT
<213> ORGANISM: Artificial Sequence
<220> FEATURE:

-continued

```
<223> OTHER INFORMATION: polypeptide sequence of a putative
      transmembrane region derived from a human IgG1 transmembrane
      domain

<400> SEQUENCE: 7

Leu Trp Thr Thr Ile Thr Ile Phe Ile Thr Leu Phe Leu Leu Ser Val
1               5                   10                  15

Cys Tyr Ser Ala Thr Val Thr Phe Phe Lys Val
            20                  25
```